(12) United States Patent
Gregorich et al.

(10) Patent No.: US 7,922,758 B2
(45) Date of Patent: Apr. 12, 2011

(54) NESTING TWISTING HINGE POINTS IN A BIFURCATED PETAL GEOMETRY

(75) Inventors: Daniel Gregorich, St. Louis Park, MN (US); Kevin Grotheim, Maple Grove, MN (US); Michael P. Meyer, Richfield, MN (US); Shawn Sorenson, Maple Grove, MN (US); Samuel Robaina, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 578 days.

(21) Appl. No.: 11/765,679

(22) Filed: Jun. 20, 2007

(65) Prior Publication Data

US 2007/0299505 A1    Dec. 27, 2007

Related U.S. Application Data

(60) Provisional application No. 60/815,950, filed on Jun. 23, 2006.

(51) Int. Cl.
*A61F 2/06* (2006.01)
(52) U.S. Cl. .......... 623/1.35; 623/1.15; 623/1.16
(58) Field of Classification Search .......... 623/1.12, 623/1.15–1.16, 1.35
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |

(Continued)

FOREIGN PATENT DOCUMENTS

CA    2220864    7/1999

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — David Isabella
*Assistant Examiner* — Seema Swaminathan
(74) *Attorney, Agent, or Firm* — Vidas, Arrett & Steinkraus, P.A.

(57) ABSTRACT

A bifurcated stent that uses turning segments to reduce the strain at regions which bend at extreme angles. The turning segments can be placed on side branch petals or on connectors connecting the petals to the stent body. Combining the turning segments with connectors of different length and tethers provides for a stent with high flexibility that can accommodate various shaped body vessels. This design allows the bifurcation branch to extend easily, to a useful distance, and to be deployed along oblique angles. Best of all, this design avoids the problems of angularly strained side branch.

15 Claims, 26 Drawing Sheets

U.S. PATENT DOCUMENTS

| | | | |
|---|---|---|---|
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,826 B1 | 12/2001 | Vardi et al. | 623/1.35 |
| 6,334,864 B1 | 1/2002 | Amplatz et al. | 606/200 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker et al. | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |

| Publication No. | Date | Inventor | Class |
|---|---|---|---|
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1 | 12/2004 | Davidson et al. | 623/1.15 |
| 2005/0004656 A1 | 1/2005 | Das | 623/1.16 |
| 2005/0010278 A1 | 1/2005 | Vardi et al. | 623/1.35 |
| 2005/0015108 A1 | 1/2005 | Williams et al. | 606/194 |
| 2005/0015135 A1 | 1/2005 | Shanley | 623/1.11 |
| 2005/0060027 A1 | 3/2005 | Khenansho | |
| 2005/0096726 A1 | 5/2005 | Sequin et al. | 623/1.12 |
| 2005/0102021 A1 | 5/2005 | Osborne | 623/1.13 |
| 2005/0102023 A1 | 5/2005 | Yadin et al. | 623/1.15 |
| 2005/0119731 A1 | 6/2005 | Brucker et al. | 623/1.35 |
| 2005/0125076 A1 | 6/2005 | Ginn | 623/23.65 |
| 2005/0131526 A1 | 6/2005 | Wong | 623/1.15 |
| 2005/0149161 A1 | 7/2005 | Eidenschink et al. | 623/1.11 |
| 2005/0154442 A1 | 7/2005 | Eidenschink et al. | 623/1.11 |
| 2005/0154444 A1 | 7/2005 | Quadri | 623/1.13 |
| 2005/0183259 A1 | 8/2005 | Eidenschink et al. | 29/508 |
| 2005/0209453 A1 | 9/2005 | Shaked | 623/1.11 |
| 2005/0228483 A1 | 10/2005 | Kaplan et al. | 623/1.15 |
| 2006/0036315 A1 | 2/2006 | Yadin et al. | 623/1.35 |
| 2006/0041303 A1 | 2/2006 | Israel | 623/1.11 |
| 2006/0079956 A1 | 4/2006 | Eigler et al. | 623/1.35 |
| 2006/0173528 A1 | 8/2006 | Feld et al. | 623/1.15 |
| 2006/0271160 A1* | 11/2006 | Gregorich et al. | 623/1.15 |
| 2007/0067019 A1* | 3/2007 | Miller et al. | 623/1.16 |
| 2007/0067023 A1* | 3/2007 | Kveen et al. | 623/1.35 |
| 2007/0073376 A1 | 3/2007 | Krolik et al. | 623/1.11 |
| 2007/0150046 A1 | 6/2007 | Meyer | |
| 2007/0260303 A1 | 11/2007 | Hegg | |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 7/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |
| WO | 2006127127 A1 | 11/2006 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/663,111, filed Sep. 15, 2000, Davidson et al.
U.S. Appl. No. 09/614,472, filed Jul. 11, 2000, Davidson et al.
U.S. Appl. No. 09/235,996, filed Jun. 4, 1999, Vardi et al.

* cited by examiner

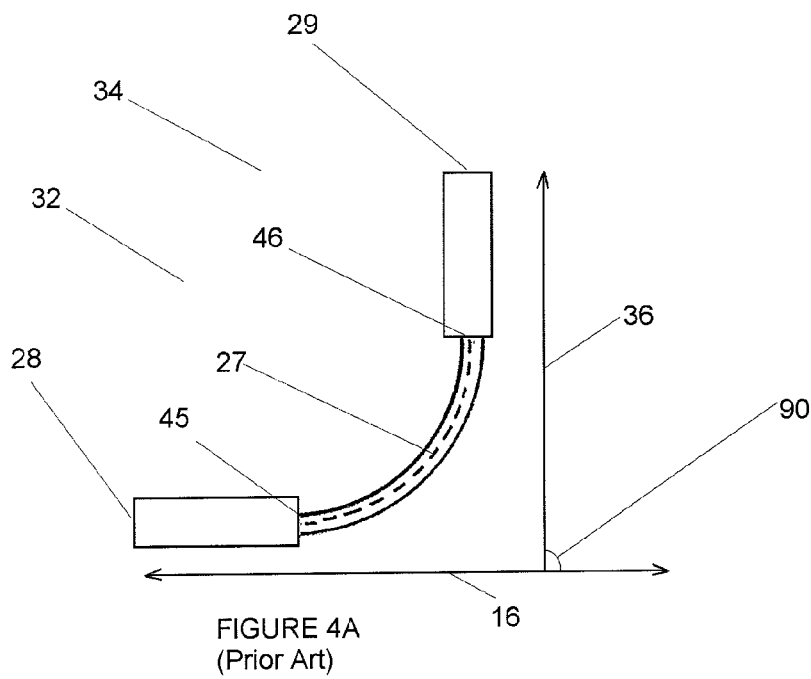
FIGURE 4A
(Prior Art)
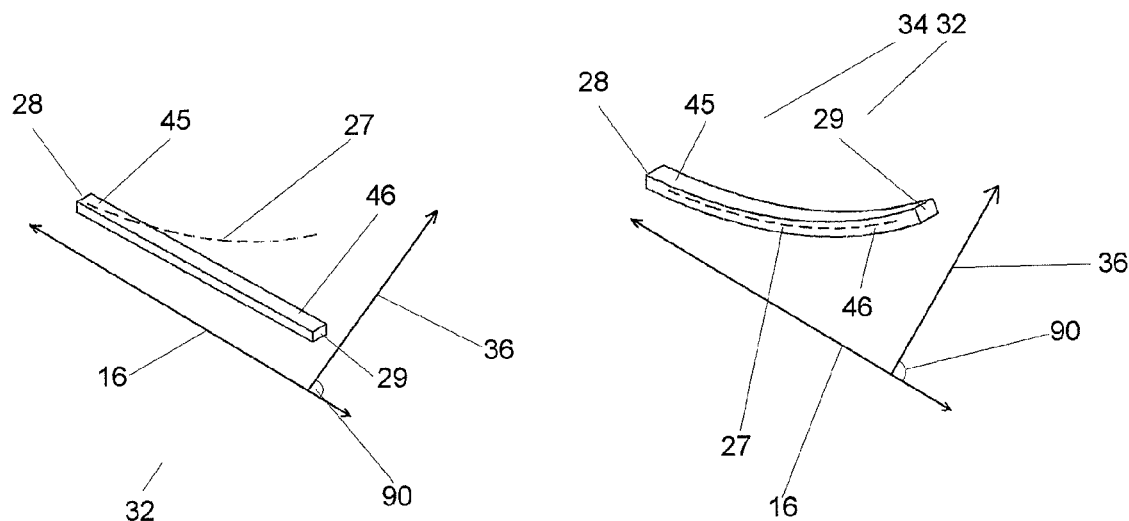
FIGURE 4B
(Prior Art)
FIGURE 4C
(Prior Art)

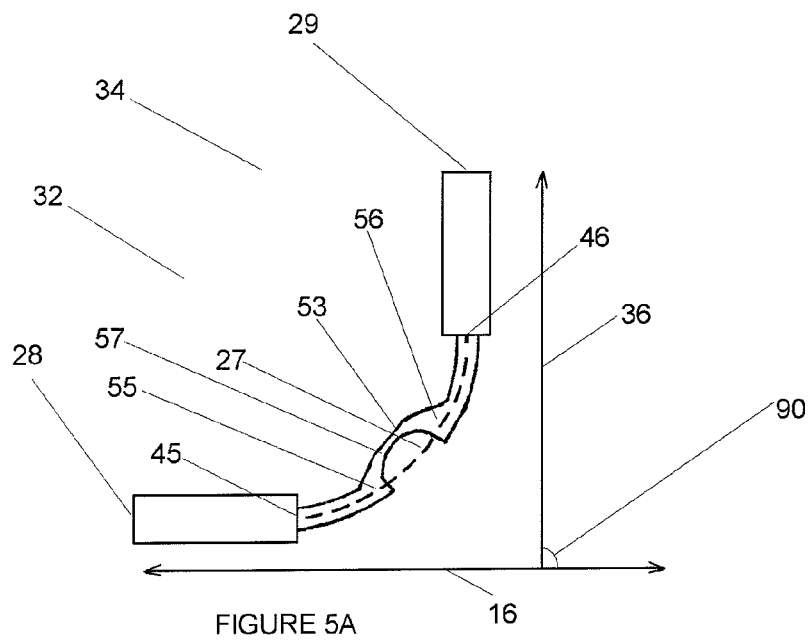
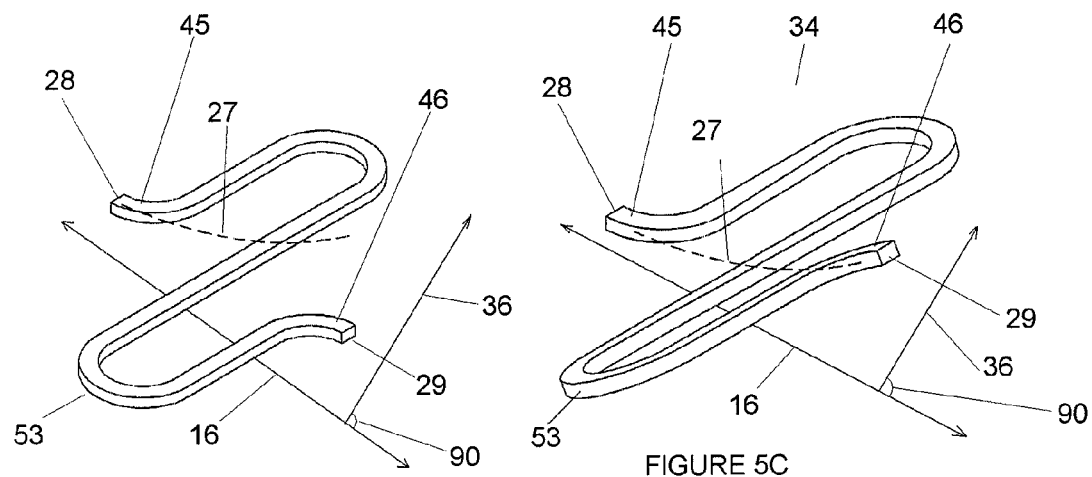
FIGURE 5A
FIGURE 5B
FIGURE 5C

               
FIG. 13a     FIG. 13b     FIG. 13c     FIG. 13d
               
FIG. 13e     FIG. 13f     FIG. 13g     FIG. 13h
     
FIG. 13i     FIG. 13j

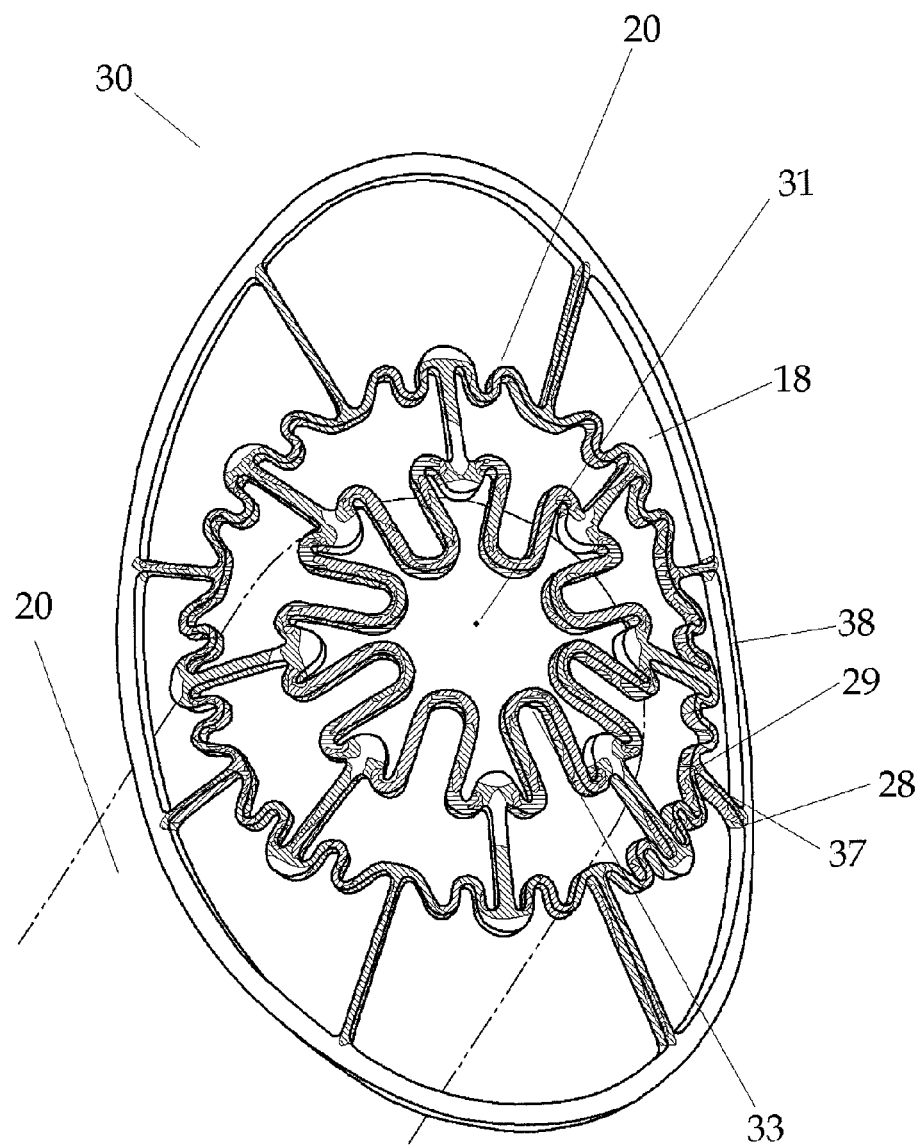
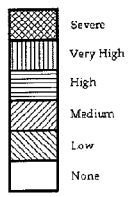
FIGURE 19

US 7,922,758 B2

NESTING TWISTING HINGE POINTS IN A BIFURCATED PETAL GEOMETRY

CROSS-REFERENCE TO RELATED APPLICATIONS

This application claims priority to U.S. Application No. 60/815,950, filed Jun. 23, 2006, the entire contents of which is incorporated herein by reference.

STATEMENT REGARDING FEDERALLY SPONSORED RESEARCH

Not Applicable

BACKGROUND OF THE INVENTION

Field of the Invention

In some embodiments this invention relates to implantable medical devices, their manufacture, and methods of use. Some embodiments are directed to delivery systems, such as catheter systems of all types, which are utilized in the delivery of such devices.

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

All US patents and applications and all other published documents mentioned anywhere in this application are incorporated herein by reference in their entirety.

BRIEF SUMMARY OF THE INVENTION

This invention contemplates a number of embodiments where any one, any combination of some, or all of the embodiments can be incorporated into a stent and/or a stent delivery system and/or a method of use. In the context of these embodiments, the term telescoping means to extend away from a stent wall in a direction different from that of the longitudinal axis of a stent. Telescoping includes but is not limited each or any combination of: extending along a linear, varied, or curved path; extending at an oblique angle from the longitudinal axis of the stent; as well as extending along a path parallel to the longitudinal axis of the stent.

At least one embodiment is directed towards a stent having an unexpanded state and an expanded state. The stent comprises a generally tubular stent body defining a first circumferential plane. The stent body defines a first lumen with a first longitudinal axis extending therethrough and the body further defines at least one side opening having a center point. The at least one side opening is in fluid communication with the first lumen. The stent also comprises a side branch assembly, the side branch assembly comprising at least two petals engaged to the stent body adjacent to the side opening. In the unexpanded state, the at least two petals are positioned substantially within the first circumferential plane. In the expanded state the at least two petals extend above the first circumferential plane and define a second lumen with a second longitudinal axis extending therethrough and form an oblique angle with the first longitudinal axis. At least one of the petals has a base, a tip, and at least one length extending between the base and the tip. The tip is located closer to the center point than the base. In the unexpanded state there is at least one ductile bend along the at least one length. The ductile bend has a first end, a second end, and a curved region between the first and second ends. The second end is located at a position on the at least one length closer to the center point than the first end is to the center point. In the expanded state the petal assumes a twisted configuration and defines a generally rounded translational arc between the base and the tip. The portion of the length between the length base and the first end of the bend and the portion of the length between the second end of the bend and the length tip both generally correspond to the translational arc. The curved region of the bend is positioned at a location different from the translational arc as the petal is positioned out of the first circumferential plane.

At least one embodiment is directed towards a stent in which there are at least four petals and the bent region of every other petal is located at the same relative position along the petal length.

At least one embodiment is directed towards a stent in which at least one petal has two lengths which are connected by a summit and the bend extends between the two lengths.

At least one embodiment is directed towards a stent in which at least one petal has a first length and a second length. Both of the lengths are connected by a summit. The first length has at least one bend and the second length has at least one more bend than the first length.

At least one embodiment is directed towards a stent having at least a portion of at least one bend on the first length which extends between at least a portion of at least two bends of the second length.

At least one embodiment is directed towards a stent having a petal which further comprises a first and a second side length each side length having first and second ends and a first and a second central length. Each central; length has first and second ends. The two side lengths extend the full length of the petal and are engaged to each other by their first ends. The two central lengths are engaged to each other by their first ends at a position farther from a center point of the side opening of than the first ends of the side lengths. The first central length and the first side length are engaged to each other at their second ends. The second central length and the first side length are engaged to each other at their second ends. The first side length also has at least one bend extending away from the petal. The first central length has at least one bend extending in the opposite direction of the bend in the first side length. The second side length has at least one bend extending away from the petal. The second central length has at least one bend extending in the opposite direction of the bend in the second side length.

At least one embodiment is directed towards a stent having a second central length which has at least two bends and at least a portion of the at least one bend of the first central length extends in between the two bends.

At least one embodiment is directed towards a stent further comprising a plurality of petals in which the second side length of each petal has at least two bends and at least a portion of at least one bend of the first side length of an adjacent petal extends in between the at least two bends of the second side length.

At least one embodiment is directed towards a stent having an unexpanded state and an expanded state. The stent comprises a generally tubular stent body defining a first circumferential plane. The stent body defines a first lumen with a first longitudinal axis extending therethrough. The stent body further defines at least one side opening, the at least one side opening in fluid communication with the first lumen. The stent also has a side branch assembly comprising at least two connectors and at least two petals. The at least two connectors connect the at least two petals to the stent body adjacent to the side opening. In the unexpanded state, at least one of the at least two connectors has at least one ductile bend and the at least two petals are positioned substantially within the first circumferential plane. In the expanded state, the at least two petals extend above the first circumferential plane and define a second lumen with a second longitudinal axis extending therethrough. The second lumen forms an oblique angle with the first longitudinal axis. At least one of the petals also has at least one length. At least one of the connectors has a curved region between the stent body and the petal. The curved region is between a first end and a second end. The second end is located at a position on the connector closer to the center point than the first end. In the expanded state, the connector assumes a twisted configuration and defines an at least partially rounded translational arc between the stent body and the petal. The portion of the connector between the stent body and the first end of the bend and the portion of the connector between the second end of the bend and the petal both generally correspond to the translational arc. The curved region of the bend is positioned at a location different from the translational arc as the petal is positioned out of the first circumferential plane.

At least one embodiment is directed towards a stent having the connector comprise a plurality of bends, the bends being longest closest to the stent body and progressively shortening as their proximity to the at least one petal increases.

At least one embodiment is directed towards a stent in which there is a plurality of connectors. Each connector connects the stent body to one of a plurality of petals. At least two connectors have different numbers of bends.

At least one embodiment is directed towards a stent having a plurality of connectors each connecting one of a plurality of petals to the stent body. In the expanded state one petal being an acute petal extending at a most acute angle relative to the first longitudinal axis and one being an obtuse petal extending at a most obtuse angle relative to the first longitudinal axis. The connector of the acute angle having more bends than a connector of the obtuse angle.

At least one embodiment is directed towards a stent in which the side opening has a perimeter and further comprising a plurality of petals connected by connectors positioned along the perimeter at positions other than those of the obtuse and acute petal connectors. The plurality of connectors has more bends than the obtuse petal and fewer bends than the acute connector. The number of bends on the plurality of connectors increases progressively with proximity to the acute petal connector.

At least one embodiment is directed towards a stent having at least one sidemost petal connector located at a position on the perimeter midway between the acute and obtuse petal connectors. The sidemost connector also has a highly twisted portion. The other connectors have progressively less twisted portions as they are positioned farther away from the sidemost connector.

At least one embodiment is directed towards a stent in which there are a plurality of connectors each connecting one of a plurality of petals to the stent body. In the expanded state one is an acute petal and extends at a most acute angle relative to the first longitudinal axis. Also in the expanded state one is an obtuse petal and extends at a most obtuse angle relative to the first longitudinal axis. The connector of the acute petal has fewer bends than the connector of the obtuse petal. In the expanded state the obtuse petal is longer than the acute petal.

At least one embodiment is directed towards a stent in which all of the connectors have bends and lengths between the bends which are positioned at a relatively perpendicular angle to an axis extending from the center of the side opening to the stent body.

At least one embodiment is directed towards a stent having an unexpanded state and an expanded state. The stent comprises a generally tubular stent body which defines a first circumferential plane and a first lumen with a first longitudinal axis extending therethrough. The body further defines at least one side opening in fluid communication with the first lumen. The stent also comprises a side branch assembly having at least three connectors and at least three petals. The at least three connectors connect the at least three petals to the stent body adjacent to the side opening. In the unexpanded state, the at least three petals are positioned substantially within the first circumferential plane. In the expanded state the at least three petals extend above the first circumferential plane and define a second lumen with a second longitudinal axis extending therethrough. The second lumen in the expanded state forms an oblique angle with the first longitudinal axis. The plurality of petals comprises an acute petal, an obtuse petal, and at least one other petal. The acute petal extends at a most acute angle relative the first longitudinal axis. The obtuse petal extends at a most obtuse angle relative the first longitudinal axis. The obtuse petal connects to at least one other petal by a tether with a length. The acute petal is connected to at least one other petal by a tether with a length.

At least one embodiment is directed towards a stent in which the length of the tether connected to the obtuse petal is longer than the length of the tether connected to the acute petal.

At least one embodiment is directed towards a stent comprising at least four petals in which every petal is connected to an adjacent petal by a tether. The tether connected to the acute petal is the shortest tether. The tether connected to the obtuse petal is the longest. The tether lengths progressively increase in length by proximity to the obtuse petal.

At least one embodiment is directed towards a stent in which the tether on the acute petal is connected at a point closer to the connector than in any other petal. The tether on the obtuse petal is connected at a point further away from the connector than in any other petal. The tether connection locations progressively get closer to the connector by proximity to the acute petal.

BRIEF DESCRIPTION OF THE SEVERAL VIEWS OF THE DRAWINGS

The invention is best understood from the following detailed description when read in connection with accompanying drawings, in which:

FIG. 4A is a lateral view of a 2-dimensional image of a stent member undergoing high strain bending.

FIG. 4B is a perspective view of a stent member prior to undergoing high strain bending.

FIG. 4C is a perspective view of a stent member undergoing high strain bending.

FIG. 5A is a lateral view of a 2-dimensional image of a stent member undergoing low strain twisting.

FIG. 5B is a perspective view of a stent member prior to undergoing low strain twisting.

FIG. 5C is a perspective view of a stent member undergoing low strain twisting.

FIG. 10B is a lateral view a side branch assembly which expands with low strain twisting.

FIG. 10C is a lateral view of a side branch assembly which expands with low strain twisting.

FIGS. 13a-13j are images of different kinds of connectors.

FIG. 17 is a lateral view of an unexpanded side branch assembly which has longer tethers on the high strain side of the side branch than on the low strain side by.

FIG. 18 is a lateral view of an unexpanded side branch assembly which has tethers positioned further away form the center point on the high strain side of the side branch than on the low strain side by.

FIG. 19 is a perspective view of the stress levels of a side branch assembly connected to a main stent body by straight connectors when beginning expansion.

DETAILED DESCRIPTION OF THE INVENTION

Figure 1:
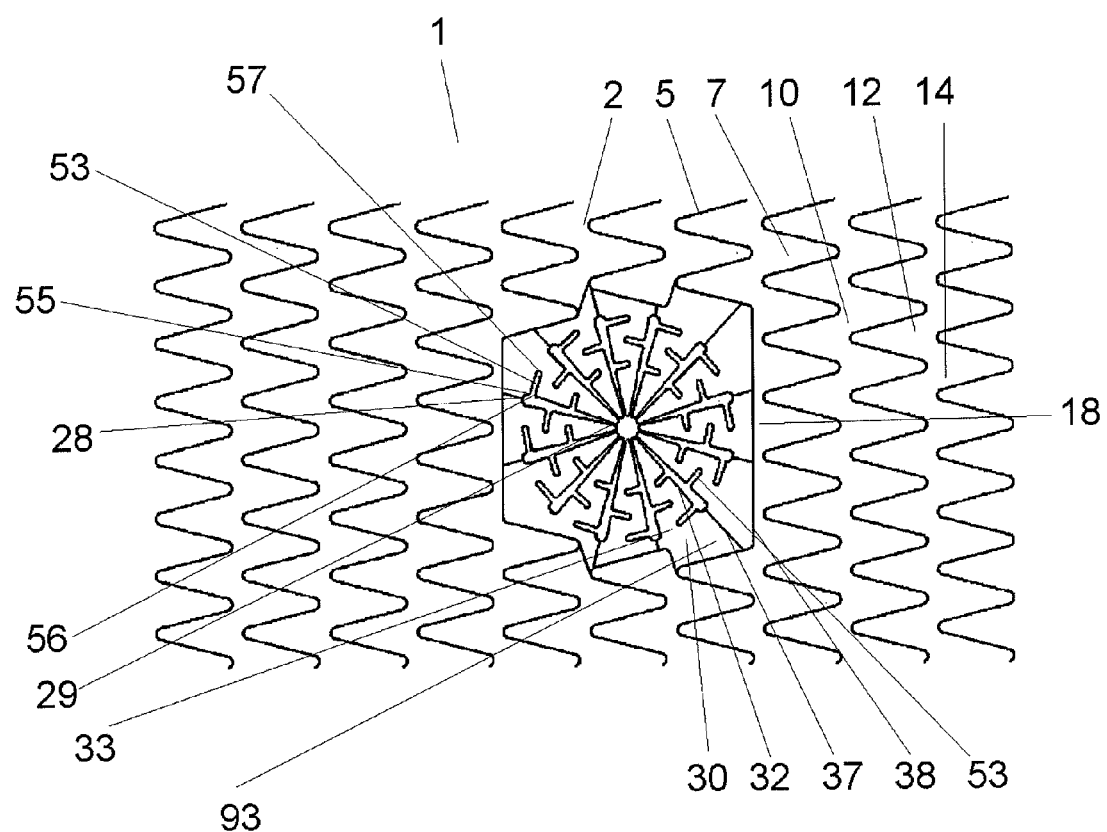
FIG. 1 is a lateral view of an unexpanded bifurcated stent with a petal type side branch assembly in which the petals have turning segments.

The invention will next be illustrated with reference to the figures wherein the same numbers indicate similar elements in all figures. Such figures are intended to be illustrative rather than limiting and are included herewith to facilitate the explanation of the apparatus of the present invention.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Figure 2:
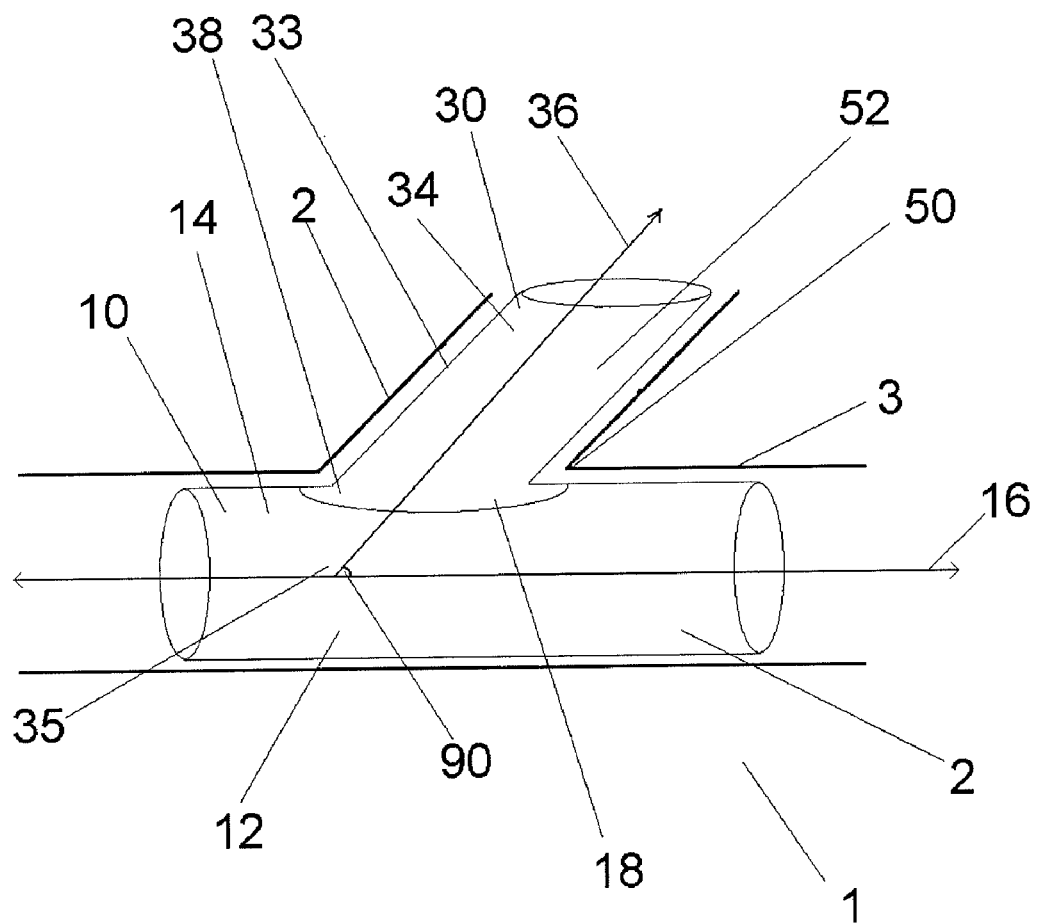
FIG. 2 is perspective view of the bifurcated stent after expansion.

Referring now to FIG. 1 there is shown an embodiment featuring an unexpanded substantially tubular bifurcated stent 1 which comprises a first stent body 10, a side branch opening 30 along its surface, and a side branch assembly 30 adjacent to and covering at least a portion of the side branch opening 30. Although in some embodiments the side branch opening is a circular or elliptical opening the opening can define any shape. The stent 1 is typically placed on a catheter shaft and is positioned within a bifurcated body vessel. The bifurcated body vessel will have at least two branching vessel lumens, one being a first vessel lumen and one being a second vessel lumen. When deployed (as illustrated in FIG. 2), the stent 1 is oriented along a first longitudinal axis 16 through the first body vessel 3 and forms an angle oblique to a secondary longitudinal axis 36 running along the length of the second body vessel 2. For the purposes of this application, the term "oblique" refers to an angle of greater than zero degrees, such as an angle of between about 1 and about 180 degrees. An oblique angle explicitly includes angles of about 90 degrees.

When the stent is unexpanded, the side branch assembly 30 is positioned adjacent to the second vessel lumen and is engaged to the first stent body 10 by at least one connector 37 at an engagement region 93. The surface of the first stent body 10 defines a first circumferential plane 12. In the unexpanded state, the side branch assembly 30 is positioned substantially along the first circumferential plane 12.

Side branch assembly 30 in FIG. 1 features two or more projecting members 33 which are sometimes referred to as petals or expansion petals which are connected by the connectors 37 to the first stent body 10. Although FIG. 1 shows twelve projecting members, embodiments of this invention can have two or more petals. When expanded, (as shown in FIG. 2) the petals bend out of the first circumferential plane 12 and define the second lumen 34 which is in fluid communication with the first lumen 14 and extends into the second body vessel 2 along a second longitudinal axis 35 at an oblique angle.

Figure 3:
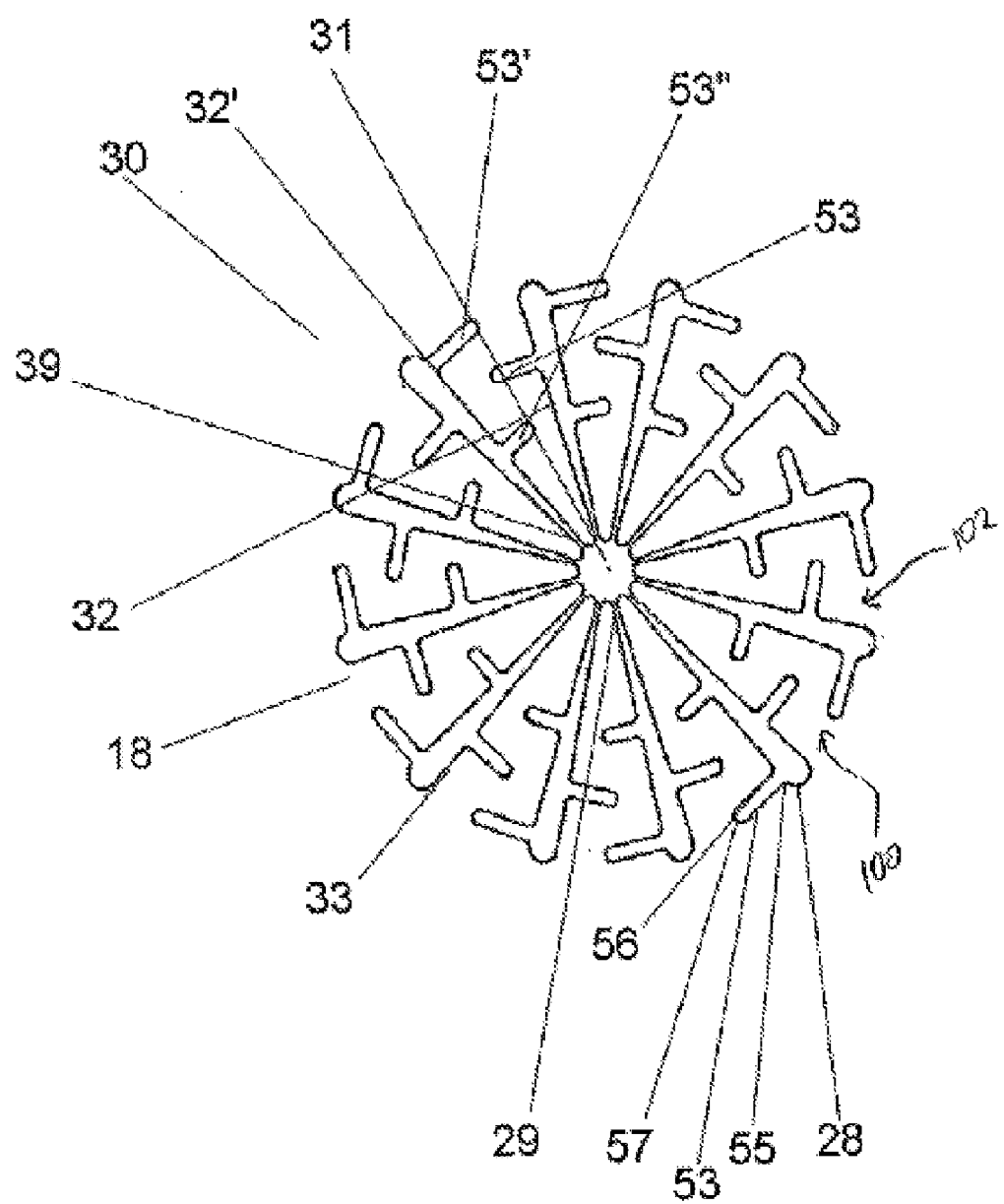
FIG. 3 is a lateral view of a side branch assembly having petals with turning segments.

Referring now to FIG. 3 there is shown one embodiment of an unexpanded side branch assembly 30 having at least one petal 33 with a length 32 generally extending towards a center point 31 of the side branch opening 18. In some embodiments, there will be two or more petal lengths 32 connected by a petal summit 39. The petal length 32 has a ductile turning segment or bend 53. When the side branch assembly 30 expands, the turning segment 53 twists in addition to just bending, allowing the petal length 32 to deploy without high stress bending. Having one or more turning segments 53 positioned at various locations on the petal length 32 allows the petal 33 to assume additional non-linear configurations.

A first half 100 of the petal is shown at 100 and a second half of the petal is shown at 102.

As illustrated in FIGS. 4A, 4B and 4C, when a petal length 32 designed according to the PRIOR ART is bent at an oblique or extreme angle 90 to form the second lumen 34, the bent petal will generally be congruent with a translational arc 27 defining a generally curved path starting from a point located at the beginning of the bend 55 and the end of the bend 56. As used in this application, the term translational arc 27 is not a mathematical formula defining the vectors of the length 32 but instead is a general term used to describe a generally curved path or a generally rounded angular path drawn from the base 28 to the tip 29. FIG. 4B shows the length prior to bending. FIGS. 4A and 4C show the length after bending.

The beginning of the bend 45 and the end of the bend 46 are both located at positions along the length 32 between the base of the length 28 and the tip of the length 29, the beginning of the bend 45 being closer to the base than the end of the bend 46. When a petal length 32 bends along a translational arc 27, the bending can be stressful and require significant energy to perform. This is the case in embodiments such as that illustrated in FIG. 4 where the portion of the length closest to the base 28 remains parallel with the longitudinal axis 16 of the first lumen and the portion of the length closest to the tip remains parallel with the longitudinal axis 36 of the second lumen 34. This is also the case in embodiments where the entire petal length 32 extends at least one angle relative to the first longitudinal axis 16. This high energy description not only applies to petal lengths but also applies to straight connectors connecting petals or side branch assemblies to stent bodies.

Figure 6:
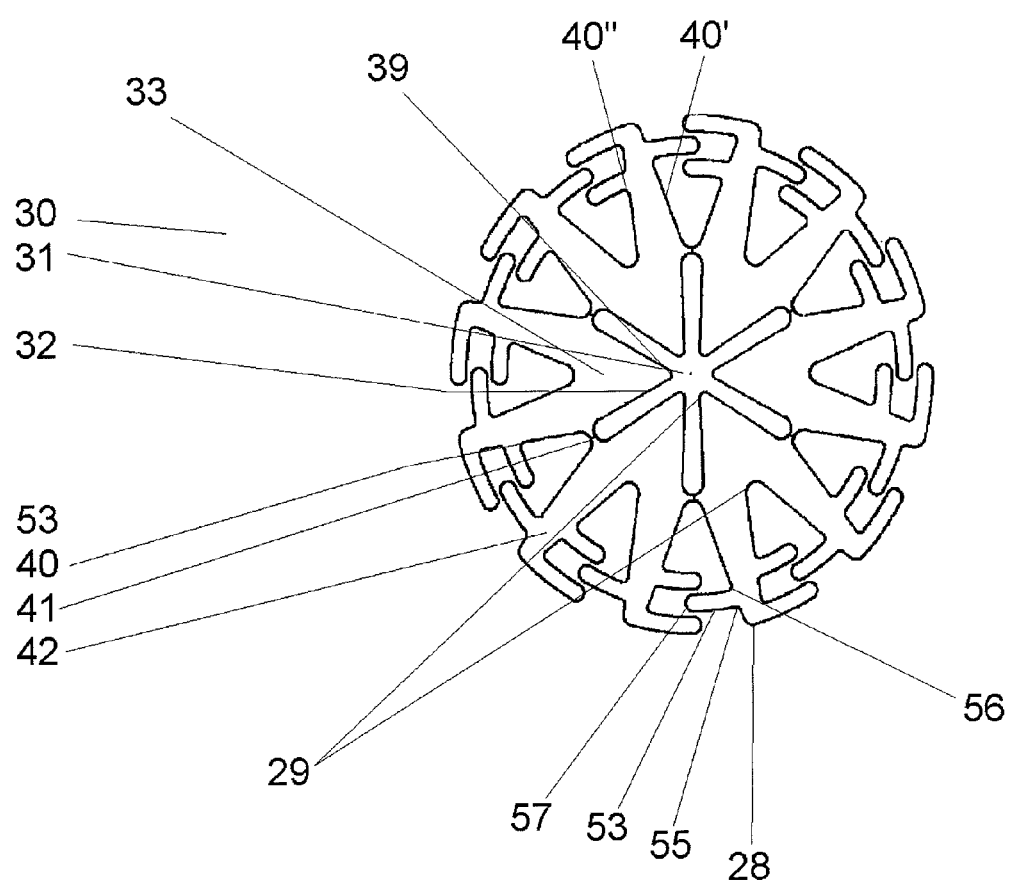
FIG. 6 is a lateral view of a side branch assembly of petals which have an outer ring with turning segments.
Figure 7:
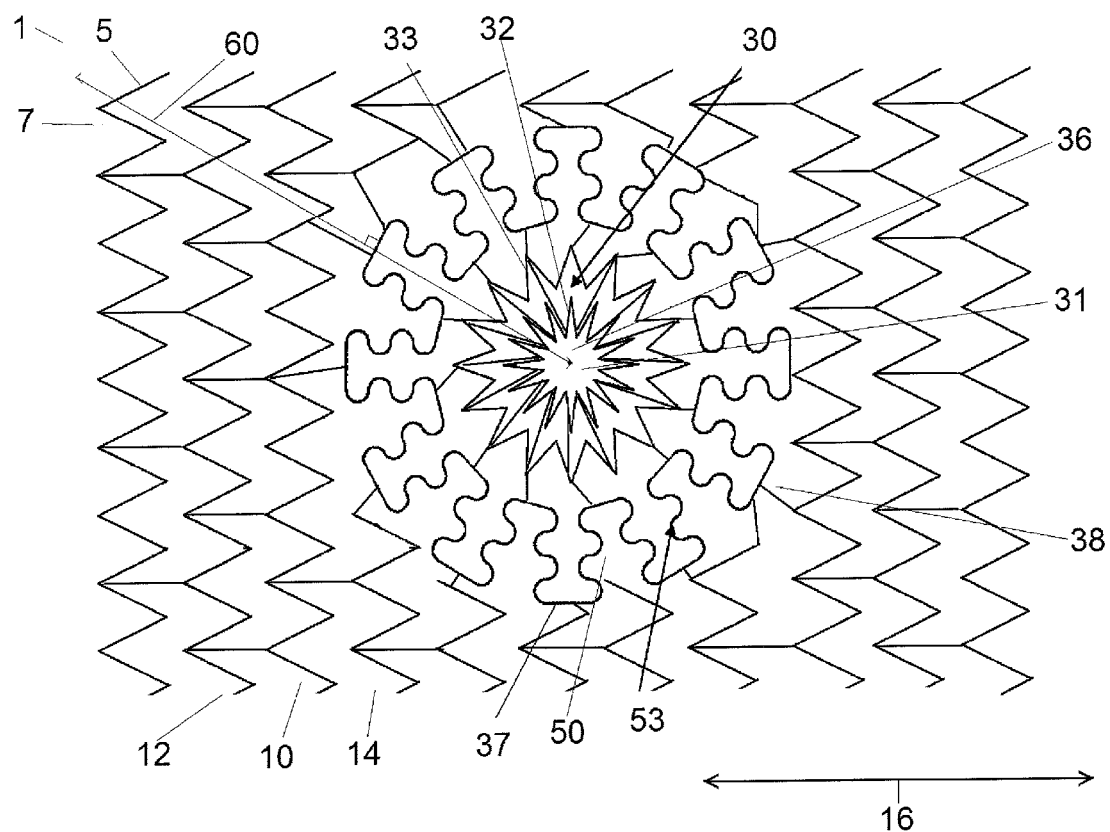
FIG. 7 is a lateral view of a side branch assembly of petals which have an outer ring with turning segments.

In contrast as shown in FIGS. 5A, 5B, and 5C, if at least one petal length 32 has at least one turning segment 53 between the base 28 and the tip 29 of the petal length 32. The turning segment 53 can twist and function as a hinge point which allows the petal length 32 to bend at the same oblique or extreme angle 90 with less stress and requiring less energy than according to the PRIOR ART configurations of FIGS. 4A, 4B and 4C. Illustrated in FIGS. 1, 3, and 6, is a view of an unexpanded petal 33 having at least one length 53 which spans from the tip 29 to the base 28 in which the turning segment 53 is a bend in the length 32 comprising a second end 56 closer to the center point 31, a first end 55 first end closer to the base 28 and a curved region 57 between the two ends (55, 56). FIG. 7 illustrates an unexpanded side branch assembly in which the connector has a turning segment. FIG. 5B shows the length prior to twisting. FIGS. 5A and 5C show the length after twisting.

In FIGS. 5A, 5B, and 5C there are shown that as the side branch assembly deploys, the petal length 32 turns away from the first longitudinal axis 16 to form the second lumen 34 and the curved region 57 twists and pivots out of the translational arc 27. Although in FIGS. 5A-5C, the translational arc appears to follow the same path as the translational arc of FIGS. 4A-4C, the path that any given translational arcs will assume is a function of the flexibility and torsional stress on the length 32 and can in places can deploy at more acute or obtuse angles and can be more angular or more rounded.

The twisting and pivoting occurring during deployment relieves the torsion stress present in the petals illustrated in FIGS. 4A-4C. This is the case in embodiments such as those illustrated in FIGS. 5A-5C where the portion of the length closest to the base 28 remains parallel with the longitudinal axis 16 of the first lumen and the portion of the length closest to the tip remains parallel with the longitudinal axis 36 the second lumen 34. This is also the case in embodiments where the entire petal length 32 extends at least one angle relative to the first longitudinal axis 16. This low energy description not only applies to petal lengths but also applies to connectors with turning segments which connect petals or side branch assemblies to stent bodies. As a rule, the lower the stress imposed on the petal length 32, the less energy is required to bend the length 32, the less likely the length is to break while bending, and the easier it is to deploy and form the second lumen 34. Multiple turning segments on a given petal length allows for the deployment of second lumens with non-linear, curved, or irregular shapes and capable of having multiple turns and curves.

In one embodiment, the turning segments are positioned along the petal length 32 at different distances from the center point 31. In at least one embodiment, the positioning of the turning segments 53 alternate and are identical in every other petal length 32. In at least one embodiment (as shown in FIG. 3), the turning segments 53 are nested. For purposes of this application the term "nested" means that the end of at least one the turning segments 53 of at least one petal length 32 is positioned at a location on the length closer to the center point 31 than a turning segment 53' on an adjacent petal length 32' and is also positioned at a location on the length farther from the center point 31 than a turning segment 53" on the same adjacent petal length 32. In at least one embodiment at least two turning segments 53 have different lengths. And in at least one embodiment at least two turning segments 53 extend away from their respective petal length 32 at different angles.

Referring now to FIG. 6 there is shown an unexpanded side branch assembly 30 in which there are at least two concentric rings an inner ring and an outer ring 42. The inner ring comprises that part of the petal length 32 which extends toward the center point 31 and is not within the outer ring 42. As illustrated in FIG. 6, the inner ring can also comprise two or more pairs of petal lengths 32 extending towards the center point 31 which are connected by connected by a petal summit 39. Connected to the end of the petal length furthest from the center point 31 is an outer ring 42 which comprises at least one outer length 40. The outer ring has at least two outer lengths 40 which are connected by at least one outer summit 41. In at least one embodiment, two petal lengths 32 are connected to one outer summit 41. Some outer lengths 40 extend along the portion of the petal lengths 32 within the outer ring and some outer lengths 40 are on members which do not extend towards the petal summits 39. Although FIG. 6 illustrates a side branch assembly having two outer summits 41 for every one petal summit 39, the ratio of petal summits 39 to outer summits 41 can be 1:1 or any other ratio. As illustrated in FIG. 6, not every outer summit 42 need be connected to the inner ring.

At least one turning segment 53 can be located on none, some, or all of the petal lengths 32 and on some or all of the outer lengths 40. The turning segments 53 can be nested, angled, and positioned along either the petal lengths 32 or outer lengths 40 in the same manner as described by FIG. 3. In one embodiment, every other outer length 40" has two turning segments 53 and the adjacent outer length 40' has one turning segment nested within the two segments of the adjacent outer length.

The deployment of the petals 33 can also be facilitated by the presence of ductile turning segments 53 on the connectors 37 connecting the petal lengths 32 to the first stent body 10 as illustrated in FIG. 7. The presence of turning segments on connectors allow the connectors to undergo low strain twisting and pivoting in the same manner as described in the explanation of FIGS. 5A-5C. The explanation of FIGS. 5A-5C when referring to turning segments on the connectors can be best understood by respectively substituting references to the end of the connector engaged to the petal with the tip of FIGS. 5A-5C and the end of the connector engaged to the stent body with the base of FIGS. 5A-5C.

Figure 8:
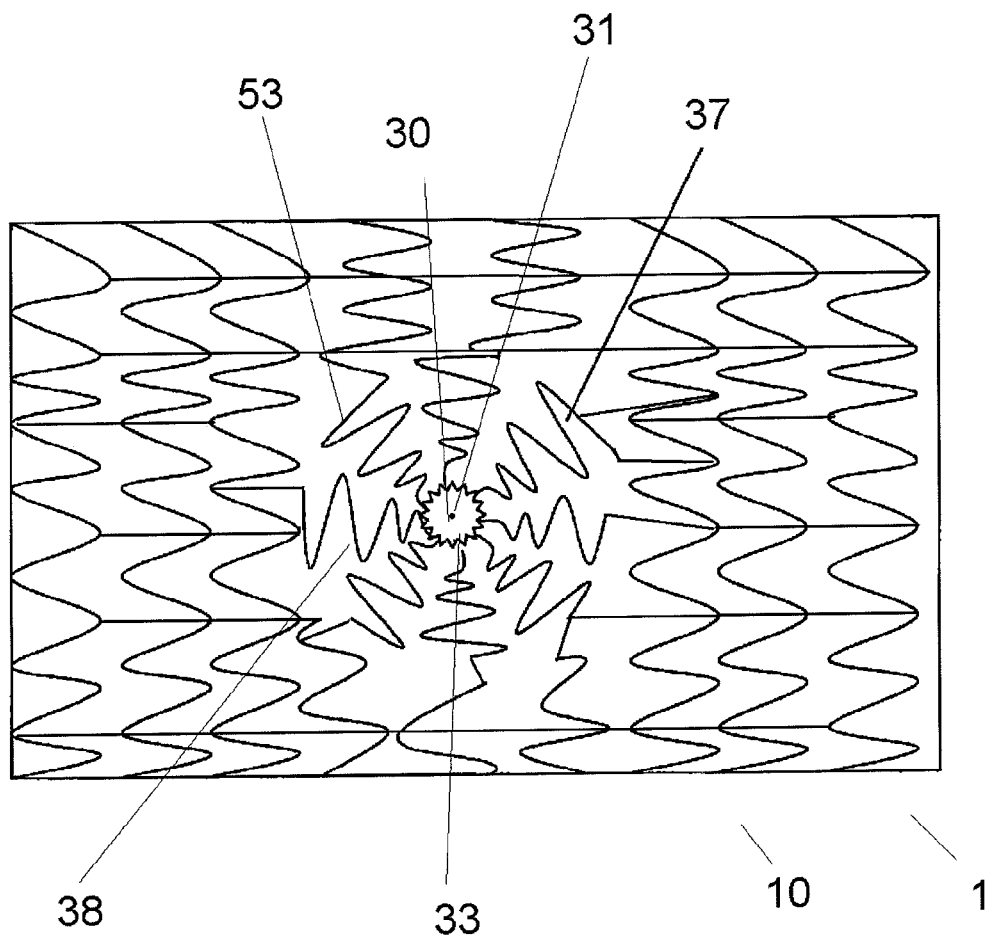
FIG. 8 is a lateral view of a side branch assembly of petals which have an outer ring with progressively widening triangular turning segments.

Now referring again to FIG. 7 it is shown that when all of the connectors surrounding the side branch assembly 30 have turning segments 53, the connectors form a flex ring 50 which can flexibly accommodate the oblique angles formed by the side branch 30 deployment. As the side branch assembly 30 deploys, the connectors 37 twist instead of just bend and receive far less axial strain during side branch extension. In one embodiment, the lengths of the turning segments are oriented in a substantially perpendicular arrangement relative to an axis 60 drawn from the center point 31. One embodiment is illustrated in FIG. 8 where at least one connector 37 has a generally triangular shape comprising at least two turning segments 53 having progressively narrowing lengths on the segments positioned closer to the petals 33. These narrowing turning segments 53 provide more conformability and flexibility at the ostium 38 of the resulting second lumen by twisting instead of bending during expansion. The longer turning segments 53 closest to the first stent body 10 are the most flexible and those closest to the petals 33 are the least flexible. This progression in flexibility allows the second lumen to be extended at angles extreme to the first longitudinal axis 16 and assures that the petals 33 project in the proper direction. The triangular shape of the connectors also is an efficient way of packaging mass which allows for a greater amount of solid surface area to be placed along the wall of the second lumen. The greater surface area allows for improved scaffolding properties and enhances the efficacy of drugs coatings on the stent.

Figure 9:
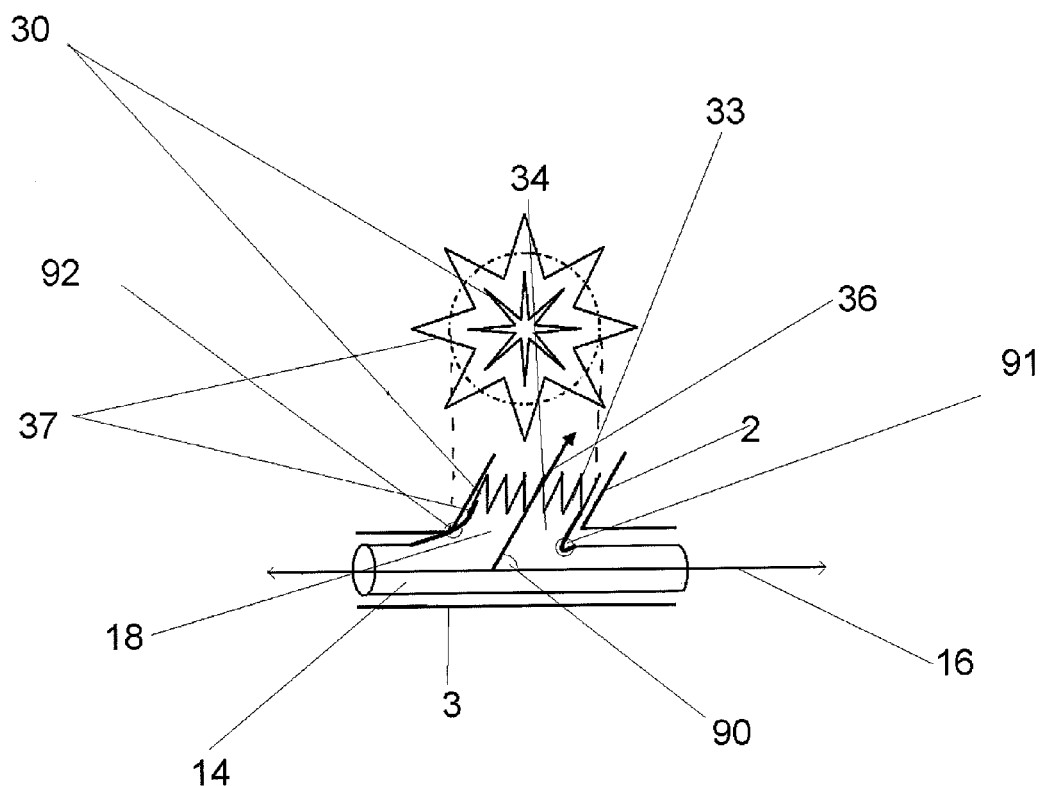
FIG. 9 is a lateral view of an expanded bifurcated stent in which a portion of the side branch assembly expands with high strain bending.
Figure 10:
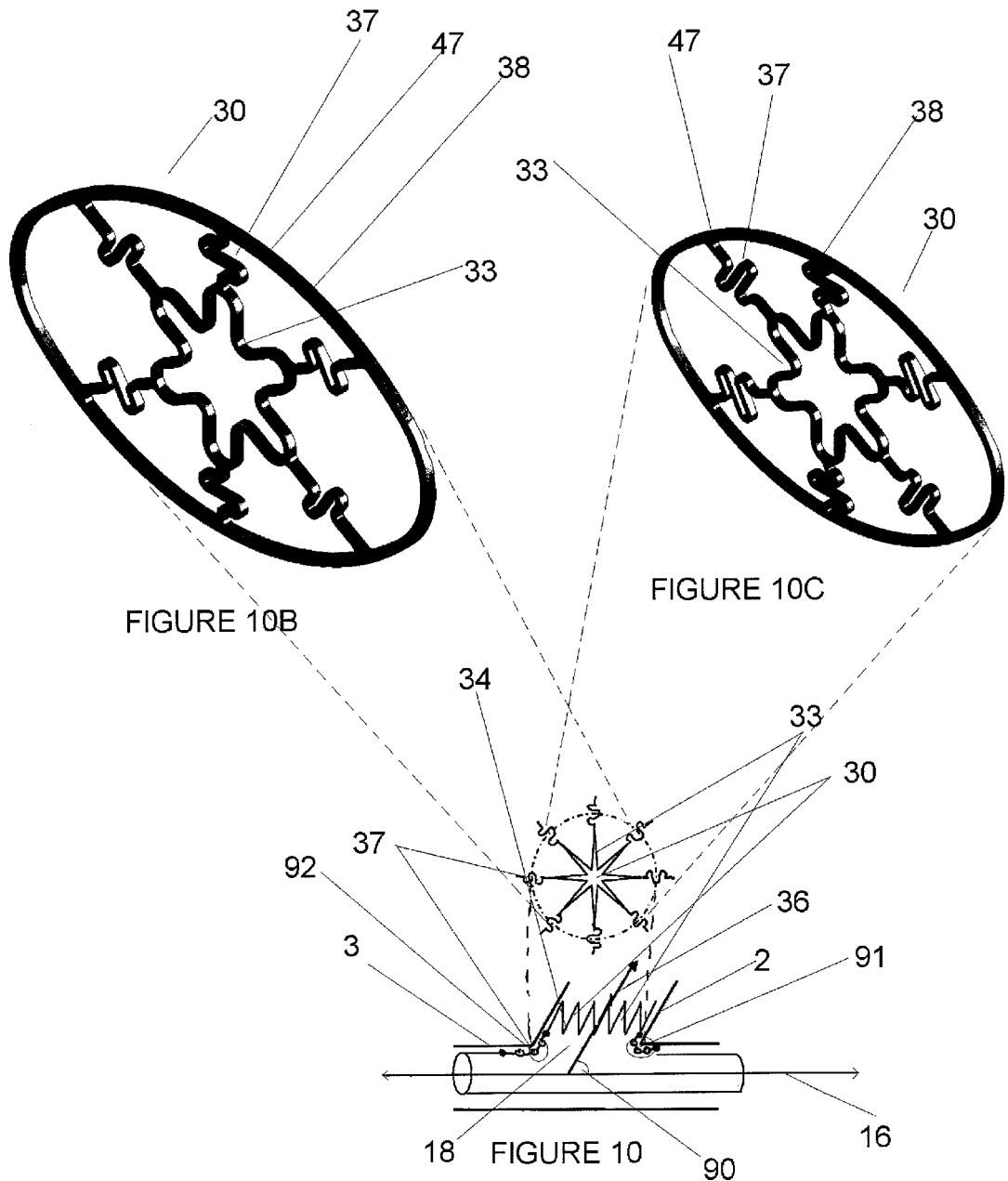
FIG. 10 is a lateral view of an expanded bifurcated stent in which a portion of the side branch assembly expands with low strain twisting.

Different regions of the second lumen will have different bending stresses. Referring now to FIG. 9, there is shown a PRIOR ART standard stent assembly having a high strain carina 91 which is a location on the stent 1 where the second lumen 34 forms the most acute angle with the first lumen 14. At the high strain carina 91, the greatest amount of axial stress is formed by expanding the side branch assembly 30. In contrast, the low strain carina 92 is a location on the stent 1 where the second lumen 34 forms the most obtuse angle with the first lumen 14. At the low strain carina 92, the least amount of axial stress formed by expanding the side branch assembly 30 occurs. In standard stent assemblies, the connector 37 connecting the petals 33 to the first stent body 10 have similar physical characteristics and do not efficiently address the different amounts of axial stress present at the two different carinas (91, 92). In contrast, as illustrated in FIG. 10, turning connectors 37 can address the high levels of axial strain at the carinas. By utilizing a number of different kinds of turning connectors 37, the different physical requirements of the various carinas (91, 92) can be addressed.

At least two embodiments of side branch assemblies 30 with turning connectors 37 capable of functioning within the stent of FIG. 10 are shown in FIGS. 10B and 10C. Although FIGS. 10B and 10C feature mounting rings 47 located at the ostium 38 for connecting the side branch assembly 30 to the main body of the stent, the mounting ring 47 is not an essential feature. Others embodiments of side branch assemblies with at least one turning connector are described below.

Figure 11:
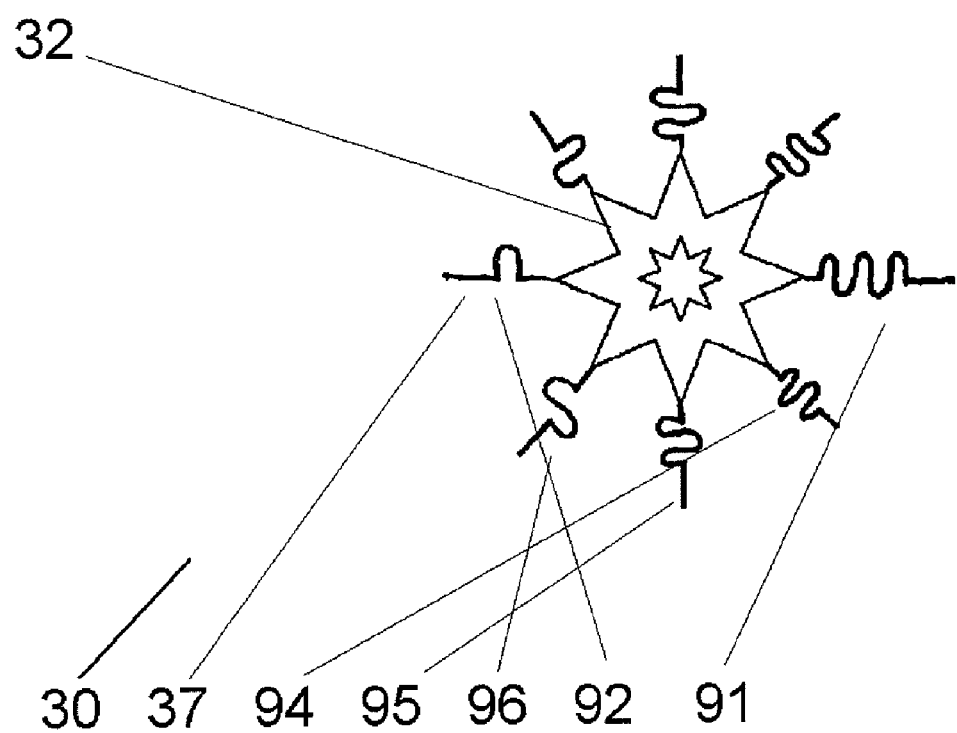
FIG. 11 is a lateral view of a stent side branch assembly having connectors with different numbers of bends.

In FIG. 11, there is shown a side branch assembly in which different kinds of turning connectors 37 are positioned at various carina points to accommodate the differing modes of bending action that occurs at different carinas. The connector at the high strain carina 91 has a greater number of bends than the connector at the low strain carina 92. One embodiment of this concept has a steadily increasing number of bends progressively positioned from the lowest strain carina 92 to the highest strain carina 91.

Figure 12:
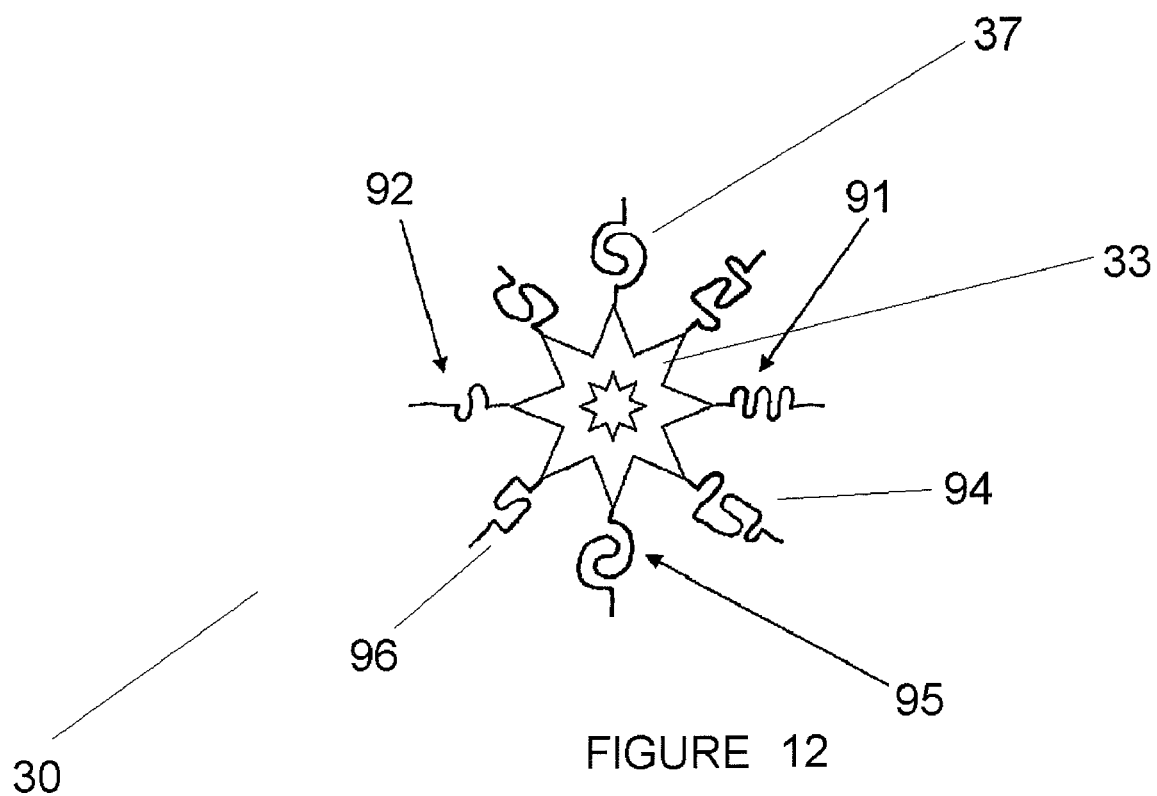
FIG. 12 is a lateral view of a stent side branch assembly having connectors with different numbers of bends and designed to accommodate rotational strain.

Another embodiment is illustrated in FIG. 12 where the connectors are designed to address both axial and rotational strain caused by side branch expansion. The connectors 37 connecting the 94 petals adjacent to the high strain carina 91 have bends designed to address both the axial stress and the rotational stress caused by the direction of the bending occurring at this location. The connectors located halfway between the two sides of the assembly 95 have connectors designed to accommodate the rotational twisting occurring at this region. The connectors located adjacent to the low strain carina 94 are designed to accommodate lower axial and rotational stress.

Although FIGS. 11 and 12 illustrate a side branch assembly having eight petals and eight connectors, there are embodiments with greater or fewer numbers of connectors. There are a number of designs that turning connectors can have some of which are illustrated in FIGS. 13*a*-13*j* and are named as follows:

13*a*: single lateral turning connector. 13*b*: double bilateral turning connector. 13*c*: triple bilateral turning connector. 13*d*: quadruple bilateral turning connector. 13*e*: quintuple bilateral turning connector. 13*f*: transverse bilateral turning connector. 13*g*: diagonal bilateral turning connector. 13*h*: double bilateral rotating connector. 13*i*: double linear turning connector. 13*j*: single arced turning connector. These turning connector configurations can also be used as the bend configurations for embodiments of the petal bends disclosed in FIGS. 1-6.

Proper connector selection is governed by the following general rules: The higher the axial strain on the connector, the more bends the connector should have. The higher the rotational strain on the connector, the more of a rounded or curved shape the connector should have. The closer the connector is to the high strain carina 91 the higher the axial strain will be. The closer the connector is to the carina at the midpoint (95) between the high (91) and low (92) strain carinas, the greater the rotational strain will be.

Figure 14:
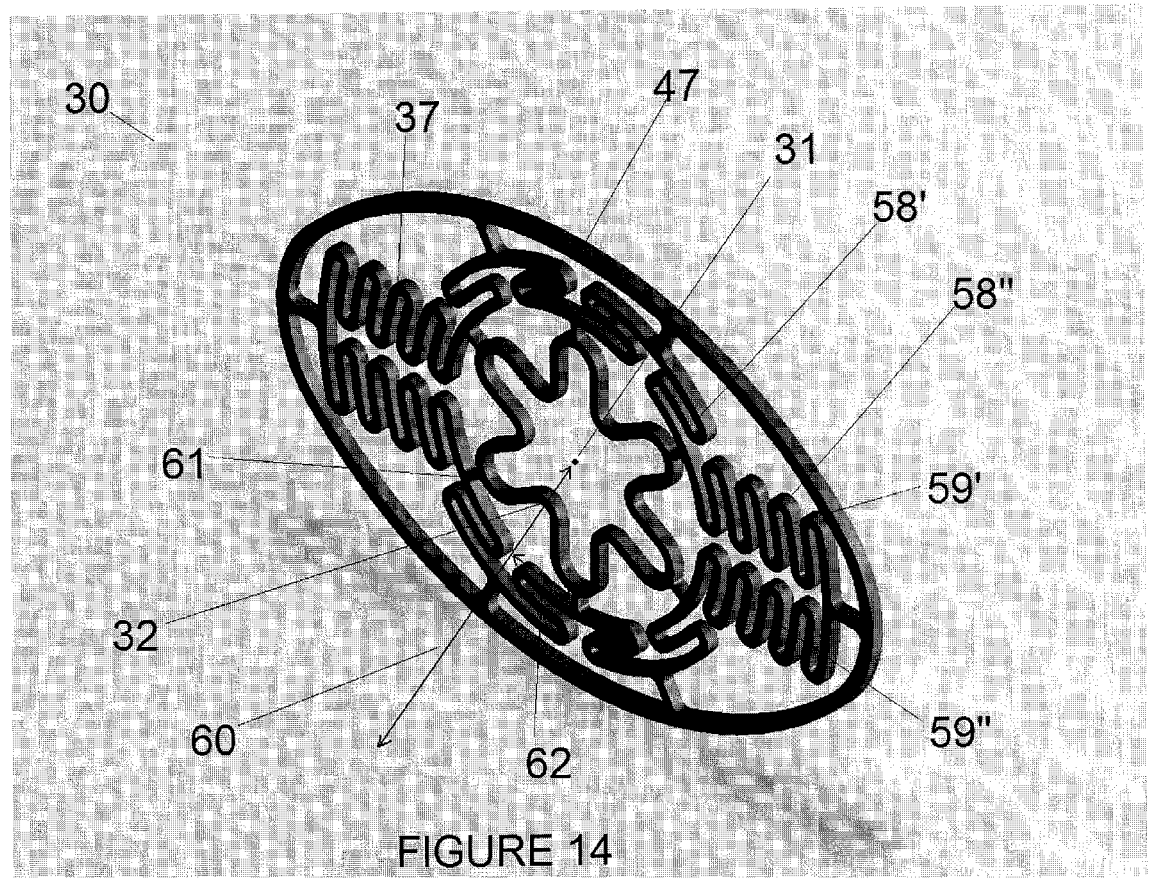
FIG. 14 is a lateral view of a side branch assembly having connectors with more than one number of turning segments.

Referring now to FIG. 14 there is shown at least one embodiment of a side branch assembly 30 for a bifurcated stent with more than one kind of turning connector 37. At least one connector 37 has more than one grouping of curved regions 57. At least some of these curved regions 57 can run in series with each other 59' and 59". Some of the connectors 37 can be connectors with a greater number of curving regions 58" and some with a lesser numbers of curing regions 58'. The connectors 37 can also comprise a connector junction 61 where adjacent connectors can be engaged to each other. The connectors 37 can engage the petals 32 at an axis offset 62 which can be offset from a radial axis 60 extending along the path between the center point 31 and the base 28 where connector 37 is engaged to a mounting ring 47 or to the main body of the stent.

In addition to those features explicitly illustrated in FIG. 14, there are at least some alternative embodiments described below. FIG. 14 shows a side branch assembly 30 covering an opening in the stent main body that is generally elliptical. The opening can in fact be circular, rounded, angular, or in any conceivable shape. FIG. 14 also illustrates the side branch assembly 30 having a mounting ring 47 suitable for engagement to the main body of the stent. The mounting ring is not an essential component and embodiments without mounting rings are possible. FIG. 14 also shows a side branch assembly 30 having 6 connectors the greater number of curved regions 58" of a connector having 8 curved regions and the lesser number of curved regions 58' having 2 curved regions. Embodiments in which some of the connectors have none, greater, equal, or lesser number of curved regions are all contemplated. FIG. 14 shows the connectors 37 having two curved region series 59' and 59" having generally parallel paths on each connector. Connectors can also have one or more than two curved region series and they can extend in generally non-parallel series as well. In addition, although FIG. 14 shows all of the connectors having a connector junction 61 not all of the connectors need have one.

Figure 15:
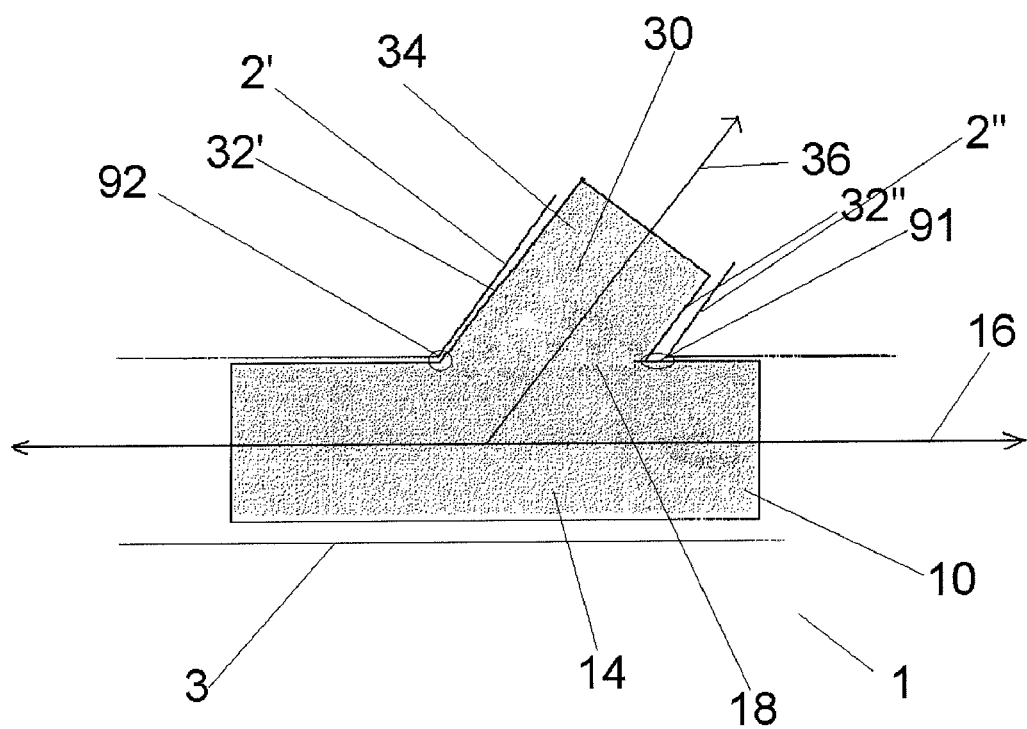
FIG. 15 is a lateral view of an expanded bifurcated stent which has a greater surface area on the high strain side of the side branch than on the low strain side.
Figure 16:
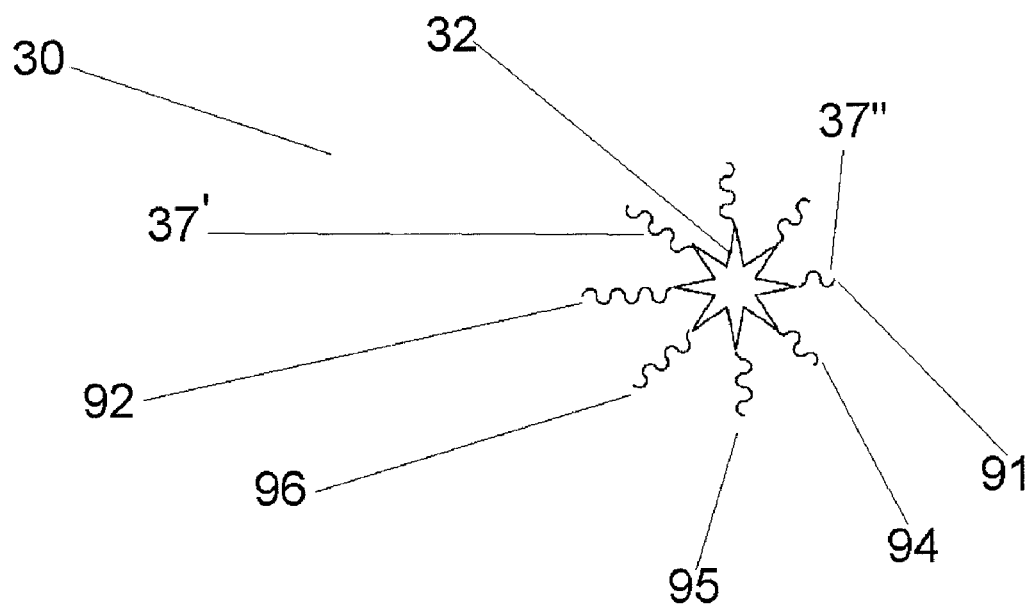
FIG. 16 is a lateral view of an unexpanded side branch assembly which will provide a greater surface area on the high strain side of the side branch than on the low strain side.

Referring now to FIG. 15 there is illustrated a bifurcated stent 1 which demonstrates that the area of the second body vessel 2' adjacent to the petal length 32' at the side of the low strain carina 92 is greater than the area of the second body vessel 2" adjacent to the petal length 32" at the high strain carina 91. One embodiment (as shown in FIG. 16) provides greater surface area to the portion of the second lumen 34 formed by the low strain petal length 32' by increasing the length and the number of turns on the connector 37' connecting the petal to the main stent body. In this embodiment, the low stress petal connector 37' has the greatest number of turns, and the number of turns on each adjacent connector progressively decreases up to the high stress connector 37". As the side branch assembly 30 expands, the increased number of turns in the connector 37" increases the distance the expanded petal can extend which increases the area of the second body vessel 2 covered by the second stent lumen 34. The number of turns in each connector 37 need not exactly match those in FIG. 16 and can be adjusted to match the particular dimensions of the second body vessel.

Figure 17:
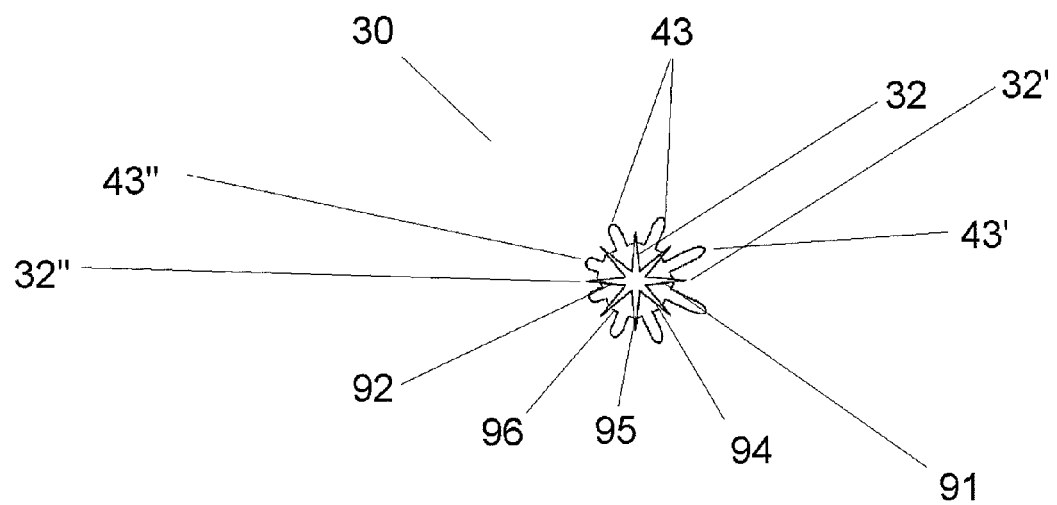

In at least one embodiment tethers can be used to control the expansion of different petals to adjust the resulting body vessel coverage. In FIG. 17 there is shown at least one embodiment in which tethers 43 of differing lengths are attached to the petals lengths 32. Long tethers 43' are attached to the petals 32' that will be on the low strain carina side 92. The tethers progressively shorten between the petals 32' closer to the high strain carina 91. The shorter tethers 43" reduce the degree to which the petal can extend during side branch expansion which reduces the overall length of that part of the second lumen 34.

Figure 18:
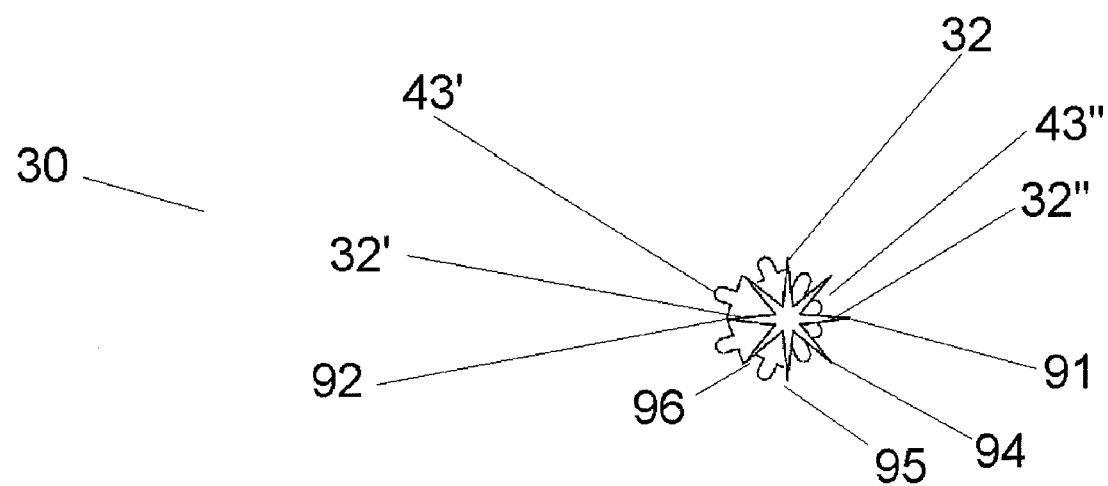

In FIG. 18 there is illustrated another embodiment utilizing tethers to properly adjust the lengths of the petals during side branch expansion. In this embodiment, the tether lengths are positioned at different points along the lengths of the petals 32. Tethers 43' are attached closer to the petal summit 39 on the petals 32' that will be on the low strain carina side 92. The tethers 43" are positioned progressively further away from the petal summit 39 on the petals 32" closer to the high strain carina 91. The lower positioning reduces the degree to which the petal can extend during side branch expansion which reduces the overall length of that part of the second lumen 34.

Figure 20:
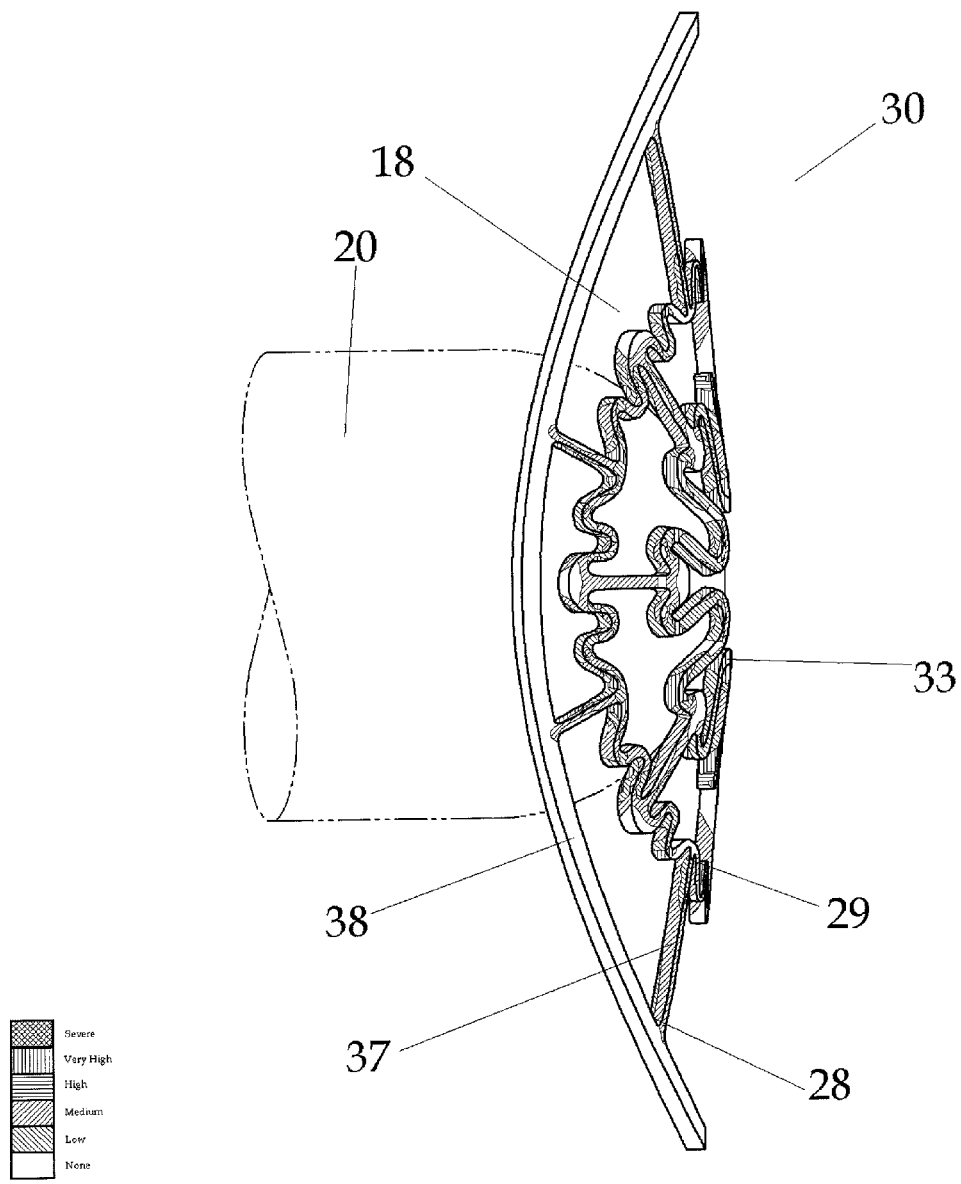
FIG. 20 is a lateral view of the stress levels of a side branch assembly connected to a main stent body by straight connectors when beginning expansion.
Figure 21:
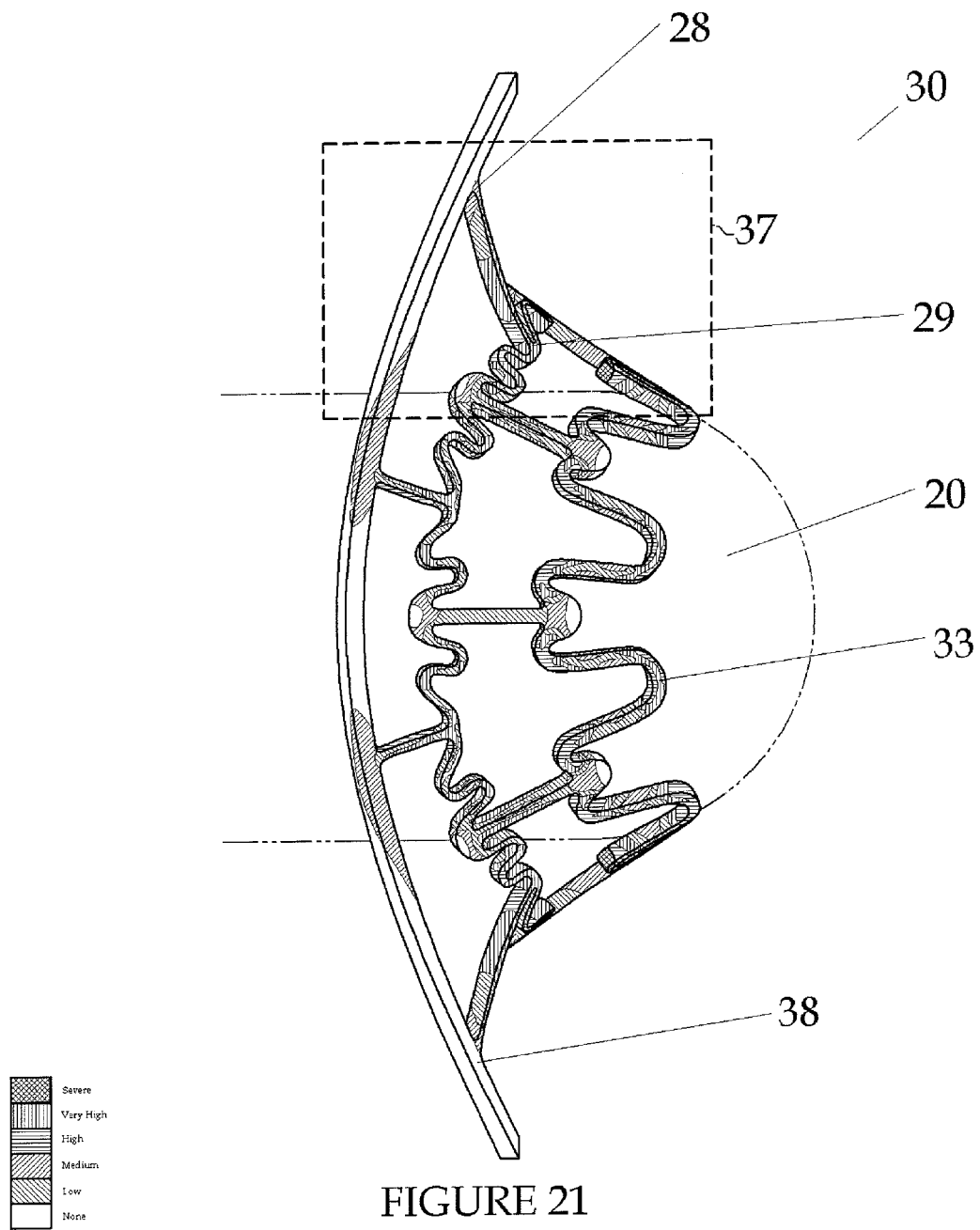
FIG. 21 is a lateral view of the stress levels of a side branch assembly connected to a main stent body by straight connectors when expanded.

Referring now to FIGS. 19 and 20 there is shown a side branch assembly 30 over a side branch opening 18 in which the side branch assembly 30 is connected to the ostium 38 by straight connectors 37. When an expansion force including but not limited to outward pressure from a balloon 20 or a self expansion mechanism pushes the side branch assembly to form the second lumen, levering stress becomes distributed unevenly along the side branch assembly 30. In particular, the straight connector 37 undergoes significant levering stress. This stress both increases the energy needed to properly deploy the side branch assembly and increases the possibility that the connector will fail resulting in a stent that is not suitable for implantation. FIG. 21 shows the same side branch assembly 30 in its expanded state and FIG. 22 is a close up of the connector 37 connecting the side branch assembly 30 to the first stent body.

FIGS. 23-26 show the same stress levels in an embodiment having curved connectors with turning segments. If contrasted with the stress diagrams of the straight connectors (FIGS. 19-22), it can be shown that the curved connectors both reduce the highest magnitude of the stress as well as the overall distribution of the stress. This same stress reducing effect is present in turning segments located along a portion of a side branch projecting member. The stress reduction can best be illustrated with detailed comparisons of close up FIGS. 22 and 26.

Figure 22:
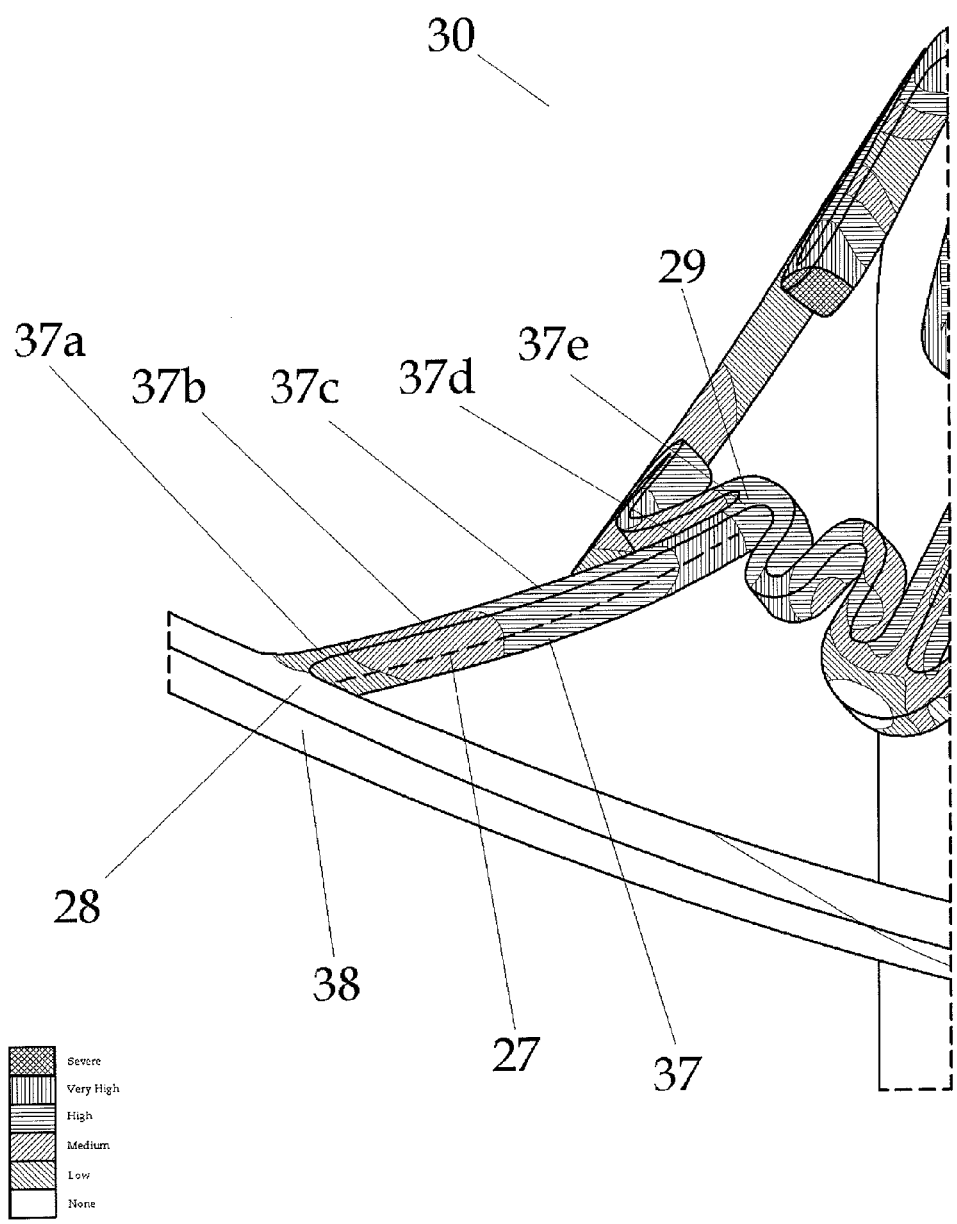
FIG. 22 is a close up lateral view of the stress levels of a straight connector connecting a side branch assembly to a main stent body when expanded.
Figure 23:
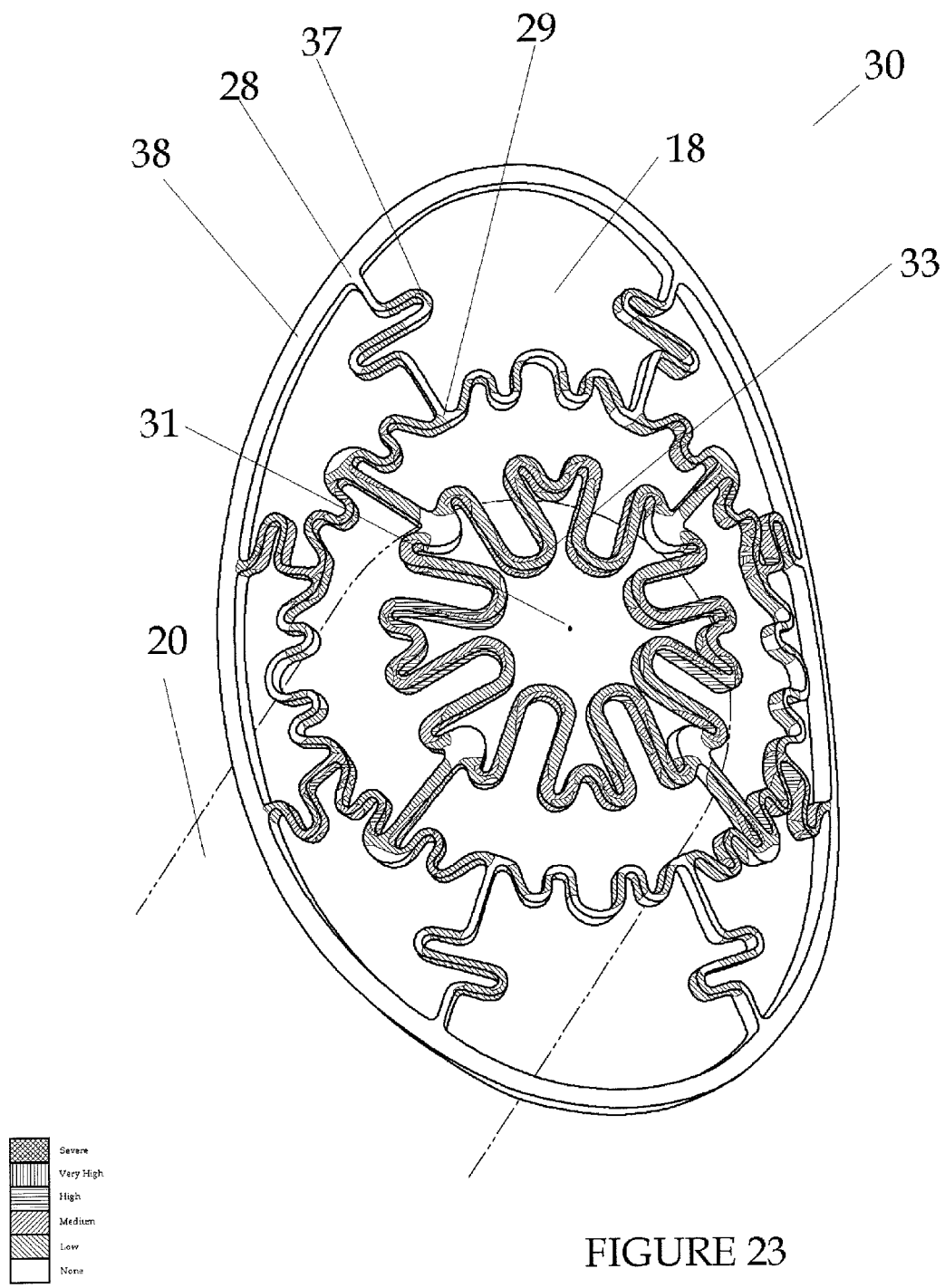
FIG. 23 is a perspective view of the stress levels of a side branch assembly connected to a main stent body by curved connectors when beginning expansion.
Figure 24:
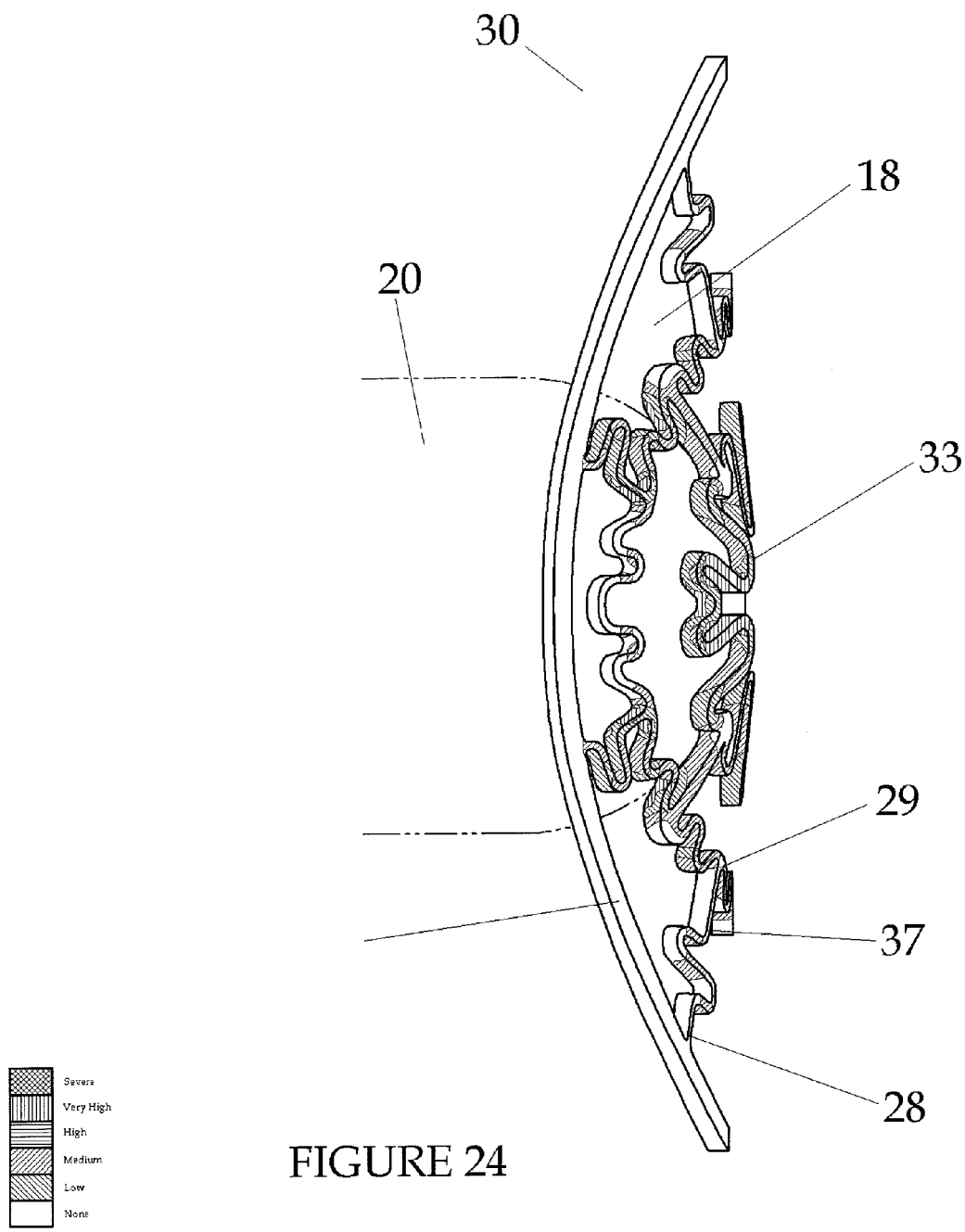
FIG. 24 is a lateral view of the stress levels of a side branch assembly connected to a main stent body by curved connectors when beginning expansion.
Figure 25:
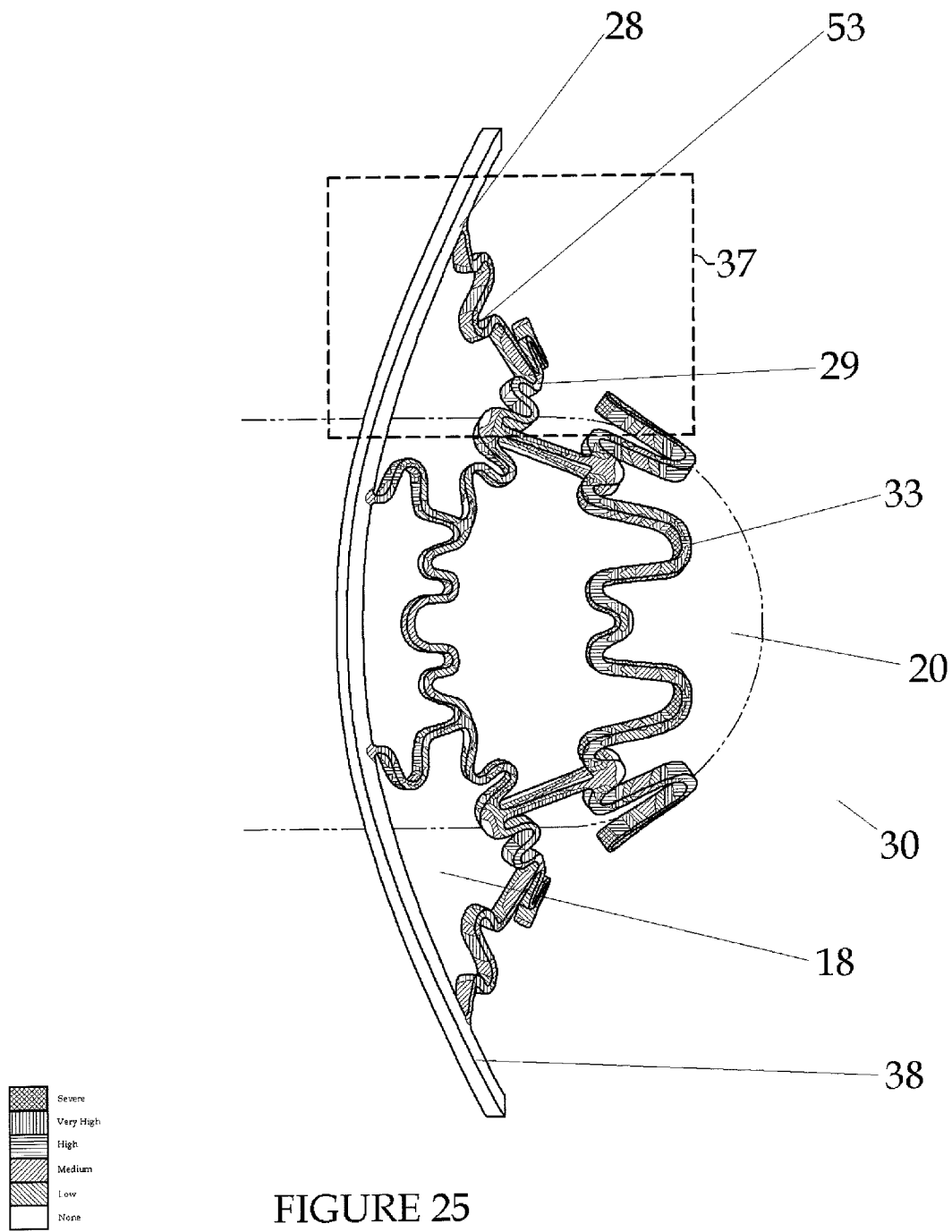
FIG. 25 is a lateral view of the stress levels of a side branch assembly connected to a main stent body by straight curved when expanded.

FIG. 22 shows a straight connector linking the side branch 30 to the ostium 38 of the stent. The stress levels extend along a range consisting of: none, low, medium, high, very high, and severe. In FIG. 22, as the connector 37 is bent along the translational arc 27, extending from the base 28, to the tip 29 are a number of sequential stress zones: first a short low stress zone 37*a*, then: a long medium stress zone 37*b*, a very long high stress zone 37*c*, a medium length very high stress zone 37*d*, and culminating in a high stress zone 37*e* at the tip 29.

Figure 26:
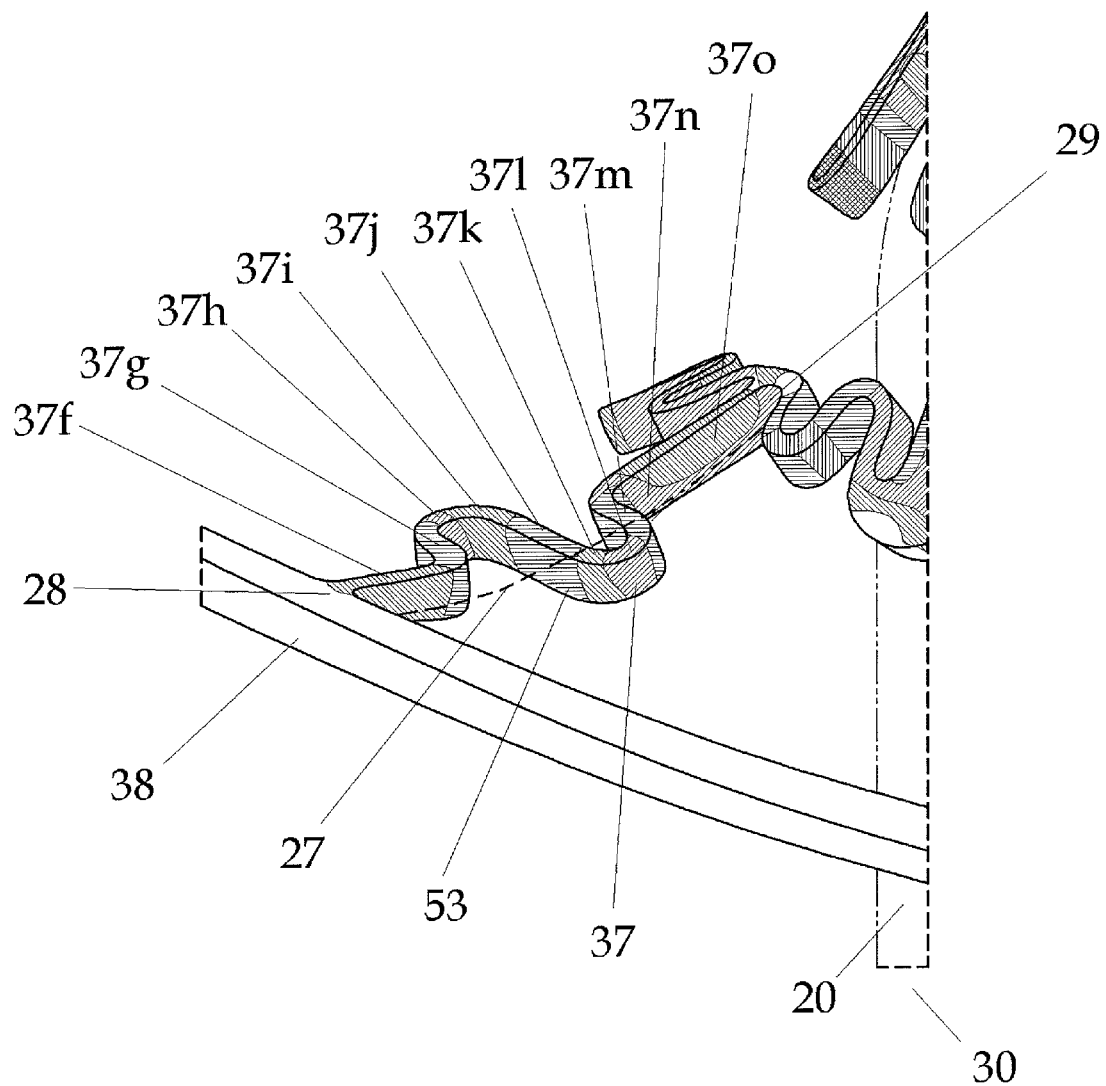
FIG. 26 is a close up lateral view of the stress levels of a curved connector connecting a side branch assembly to a main stent body when expanded.

In contrast FIG. 26 shows that at least one turning segments 53 in the connector 37 reduces both the highest magnitude of stress experienced by the connector 37 as well as the overall stress distribution over the connector 37. In FIG. 26, as the connector 37 is bent to partially follow the translational arc 27, extending from the base 28 to the tip 29 are more sequential stress zones with lower stress magnitudes extending over a greater length of the connector. Specifically, there begins a medium length low stress zone 37*f* (longer than the short low stress zone 37*a* of FIG. 22), followed by: a medium high stress zone 37*g*, a short medium stress zone 37*h*, a medium length low stress zone 37*i*, a medium length high stress zone 37*j*, a short low stress zone 37*k*, a medium length low stress zone 37*l*, a medium high stress zone 37*m*, a long medium stress zone 37*n* and culminating in a long low stress zone 37*o* at the tip 29.

Observation of FIGS. 22 and 26 shows that a much greater proportion of the overall length of the curved connector 37 in FIG. 26 undergoes medium or low stress than in the straight connector of FIG. 22. In particular, the very high zone 37*d* and high zone 37*e* close to the tip 29 in the straight connector correspond with the medium zone 37*n* and low zone 37*o* between the end of the bend 46 and the tip 29 of the curved connector. In addition, unlike in the straight connector, the curved connector has no very high stress zones.

In some embodiments the stent, its delivery system, or other portion of an assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A stent having an unexpanded state and an expanded state, the stent comprising:
    a generally tubular stent body defining a first circumferential plane, the stent body defining a first lumen with a first longitudinal axis extending therethrough, the stent body further defining at least one side opening having a perimeter, the at least one side opening in fluid communication with the first lumen; and
    a side branch assembly, the side branch assembly comprising at least two petals engaged to the stent body adjacent to the at least one side opening, in the unexpanded state, the at least two petals being positioned substantially within the first circumferential plane, in the expanded state the at least two petals extending above the first circumferential plane and defining a second lumen with a second longitudinal axis extending therethrough, the second longitudinal axis intersecting and forming an oblique angle with the first longitudinal axis,
    wherein at least one of the at least two petals comprises a first expansion petal having a base, a tip, and two halves, the first half having a first straight segment and a second straight segment, a first ductile bend and a second ductile bend, and the second half having a third straight segment, a fourth straight segment, and a third ductile bend, the first and second halves being connected to one another at the base, the base being located closer to the side opening perimeter than the tip;
    in the unexpanded state, the first, second, and third ductile bends each have a first end, a second end, and a curved region between the first and second ends, the first end being located at a position closer to the side opening perimeter than the second end, wherein each of the first, second, and third ductile bends is radially offset from the other of the ductile bends when the first expansion petal is in the unexpanded state;
    in the expanded state the ductile bends assuming a twisted configuration and defining a generally rounded translational arc between the base and the tip.

2. The stent of claim 1, wherein the first straight segment extends from the tip, the first ductile bend extends from the first straight segment, the second straight segment extends from the first ductile bend, and the second ductile bend extends from the second straight segment, the base extends from the second ductile bend, the third straight segment extends from the base, the third ductile bend extends from the third straight segment, and the fourth straight segment extends from the third ductile bend, each of the first, second, third, and fourth straight segments extending in a radial direction outwardly from the tip when the first expansion petal is in the unexpanded state.

3. The stent of claim 2, wherein the at least two petals further comprises a second expansion petal, the second expansion petal being adjacent to the first expansion petal, the second expansion petal having a base, a tip, and two halves, the first half having a first straight segment and a second straight segment a first ductile bend and a second ductile bend, and the second half having a third straight segment, a fourth straight segment, and a third ductile bend, the first and second halves being connected to one another at the base;

the first segment of the second expansion petal extending from the tip, the first ductile bend extending from the first straight segment, the second straight segment extending from the first ductile bend, and the second ductile bend extending from the second straight segment, the base extending from the second ductile bend, the third straight segment extending from the base, the third ductile bend extending from the third straight segment, and the fourth straight segment extending from the third ductile bend, each of the first, second, third, and fourth straight segments extending in a radial direction outwardly from the tip when the second expansion petal is in the unexpanded state, the base being located closer to the side opening perimeter than the tip;

the third ductile bend of the first expansion petal extending between a portion of the first and second expansion petals of the second expansion petal.

4. The stent of claim 2, wherein each of the ductile bends comprises two straight portions separated by one bent portion, the two straight portions being parallel to one another.

5. The stent of claim 4, wherein the straight portions of the first ductile bend are parallel to one another, the straight portions of the second ductile bend are parallel to one another, and the straight portions of the third ductile bend are parallel to one another.

6. The stent of claim 5, wherein the straight portions of the first ductile bend are shorter than the straight portions of the second and third ductile bends and the straight portions of the third ductile bend are shorter than the straight portions of the second ductile bend.

7. The stent of claim 6, wherein the at least two petals comprises twelve expansion petals, each expansion petal being connected to an adjacent expansion petal at a tip.

8. The stent of claim 7, wherein each of the twelve expansion petals has the same structure as the adjacent expansion petal.

9. A stent having an unexpanded state and an expanded state, the stent comprising:

a generally tubular stent body defining a first circumferential plane, the stent body defining a first lumen with a first longitudinal axis extending therethrough, the body further defining at least one side opening having a perimeter, the at least one side opening in fluid communication with the first lumen; and a side branch assembly adjacent to the side opening, the side branch assembly comprising at least two connectors and at least two petals, the at least two connectors each connecting one of the at least two petals to the stent body, in the unexpanded state, at least one of the at least two connectors having at least one ductile connector bend and the at least two petals being positioned substantially within the first circumferential plane, in the expanded state the at least two petals extending above the first circumferential plane and defining a second lumen with a second longitudinal axis extending therethrough and forming an oblique angle with the first longitudinal axis, wherein each of the at least two petals having comprises a base, a tip, and two halves, the first half having a first straight segment and a second straight segment, a first ductile petal bend and a second ductile petal bend, and the second half having a third straight segment, a fourth straight segment, and a third ductile petal bend, the first and second halves being connected to one another at the base;

the at least one ductile connector bend comprising at least one curved region being between a first end and a second end, the first end being located at a position on the connector closer to the perimeter of the side branch opening point than the second end;

in the expanded state the connector assuming a twisted configuration and defining an at least partially rounded translational arc between the stent body and the petal.

10. The stent of claim 9 in which at least one of the at least two connectors comprises a plurality of ductile connector bends, the ductile connector bend closest to the stent body having a greatest expansion away from the first end and the expansion away from the first end of each ductile bend progressively decreasing as their proximity to the at least one petal increases.

11. The stent of claim 9 in which there are a plurality of connectors each connecting the stent body to one of a plurality of petals and at least two connectors have different numbers of ductile connector bends.

12. The stent of claim 9 in which there are a plurality of connectors each connecting one of a plurality of petals to the stent body, in the expanded state one petal being an acute petal extending at a most acute angle relative to the first longitudinal axis and one being an obtuse petal extending at a most obtuse angle relative to the first longitudinal, the connector of the acute angle having more ductile connector bends than the connector of the obtuse angle.

13. The stent of claim 12 further comprising a plurality of petals connected to the stent body by connectors positioned along the perimeter at positions other than those of the connectors of the obtuse and acute petals, the plurality of connectors having more ductile connector bends than the obtuse petal connector, fewer ductile connector bends than the acute petal connector and the number of ductile connector bends on the plurality of connectors increasing progressively with proximity to the acute petal connector.

14. The stent of claim 9 in which there are a plurality of connectors each connecting one of a plurality of petals to the stent body, in the expanded state one petal being an acute petal extending at a most acute angle relative to the first longitudinal axis and one petal being an obtuse petal extending at a most obtuse angle relative to the first longitudinal axis, the connector of the acute petal having fewer ductile connector bends than the connector of the obtuse petal, in the expanded state the obtuse petal being longer than the acute petal.

15. The stent of claim 9, wherein the first straight segment extends from the tip, the first ductile petal bend extends from the first straight segment, the second straight segment extends from the first ductile petal bend, and the second ductile petal bend extends from the second straight segment, the base extends from the second ductile petal bend, the third straight segment extends from the base, the third ductile petal bend extends from the third straight segment, and the fourth straight segment extends from the third ductile petal bend, each of the first, second, third, and fourth straight segments extending in a radial direction outwardly from the tip when the at least two petals are in the unexpanded state, wherein each of the first, second, and third ductile petal bends is radially offset from the other of the ductile petal bends when the at least two petals are in the unexpanded state.

* * * * *